ns010542997B2

United States Patent
Roig et al.

(10) Patent No.: US 10,542,997 B2
(45) Date of Patent: Jan. 28, 2020

(54) DEVICES AND METHODS FOR REMOVING UNWANTED TISSUE

(71) Applicants: University of Florida Research Foundation, Inc., Gainesville, FL (US); Carlos Hondal, Coral Gables, FL (US)

(72) Inventors: Juan Carlos Roig, Ocala, FL (US); Carlos Hondal, Coral Gables, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 640 days.

(21) Appl. No.: 15/030,054

(22) PCT Filed: Oct. 23, 2014

(86) PCT No.: PCT/US2014/061973
§ 371 (c)(1),
(2) Date: Apr. 16, 2016

(87) PCT Pub. No.: WO2015/061571
PCT Pub. Date: Apr. 30, 2015

(65) Prior Publication Data
US 2016/0249931 A1    Sep. 1, 2016

Related U.S. Application Data

(60) Provisional application No. 61/951,205, filed on Mar. 11, 2014, provisional application No. 61/894,736, filed on Oct. 23, 2013.

(51) Int. Cl.
*A61B 17/50* (2006.01)
*A61B 17/122* (2006.01)
(Continued)

(52) U.S. Cl.
CPC .............. *A61B 17/122* (2013.01); *A61D 1/06* (2013.01); *A61B 2017/12004* (2013.01); *A61B 2017/1225* (2013.01); *A61B 2017/320052* (2013.01)

(58) Field of Classification Search
CPC .................. A61B 17/12; A61B 17/122; A61B 2017/12004; A61B 2017/1225; A61B 17/326; A61D 1/06
See application file for complete search history.

(56) References Cited

U.S. PATENT DOCUMENTS 3,454,009 A    7/1969 Hunnicutt
3,678,935 A    7/1972 Bronstein
(Continued)

FOREIGN PATENT DOCUMENTS

CN    102940512 A    2/2013
FR    2970637    7/2012
(Continued)

*Primary Examiner* — Melanie R Tyson
(74) *Attorney, Agent, or Firm* — Timothy H. Van Dyke; Beusse, Wolter, Sanks & Maire PLLC

(57) ABSTRACT

Devices and methods for removing tissue, which causes minimal pain or scarring. A hemostatic clamp having two arms with juxtaposeablefaces, can compress tissue between the faces of the arms so as to fuse a portion of the tissue therebetween. A locking mechanism maintains pressure on the arms until the skin is fused to create a skin tab. The unwanted tissue, such as a polydactyl digit, skin tag, or the like, can be excised with the clamp in position. When the locking mechanism is disengaged and the clamp is removed, the fused skin tab inhibits bleeding and the removal of the digit encourages any remaining underlying nerves to withdraw from the area of amputation. A related device can be used as a castration clamp to externally compress testicular-related tissues, such as ductiles, nerves, and blood vessels leading to the testicles, to castrate an animal. The castration (Continued)

clamp provides a quick, bloodless technique that eliminates the need for open wounds, which are subject to infection.

3 Claims, 28 Drawing Sheets

(51) Int. Cl.
*A61D 1/06* (2006.01)
*A61B 17/12* (2006.01)
*A61B 17/32* (2006.01)

(56) References Cited

U.S. PATENT DOCUMENTS

| | | | |
|---|---|---|---|
| D287,763 S | * | 1/1987 | Porat .......................... D24/143 |
| 5,608,382 A | * | 3/1997 | Webb ................... A61B 17/122 |
| | | | 340/5.81 |
| 5,746,748 A | | 5/1998 | Steinberg et al. |
| 6,174,309 B1 | | 1/2001 | Wrublewski et al. |
| 6,780,194 B2 | * | 8/2004 | Freedman ............ A61B 17/326 |
| | | | 606/118 |
| 6,860,179 B2 | | 3/2005 | Hopper et al. |
| 8,123,743 B2 | | 2/2012 | Arts et al. |
| 2003/0004521 A1 | | 1/2003 | Oriowski |
| 2006/0200179 A1 | * | 9/2006 | Barker ................. A61B 17/122 |
| | | | 606/157 |
| 2012/0312859 A1 | | 12/2012 | Gupta et al. |

FOREIGN PATENT DOCUMENTS

| | | | | |
|---|---|---|---|---|
| FR | 3028748 A1 | * | 5/2016 | ........... A61B 17/326 |
| FR | 3064905 A1 | * | 10/2018 | ........... A61B 17/326 |
| JP | 2004532674 A | | 10/2004 | |
| JP | 2004533881 A | | 11/2004 | |
| JP | 2005506110 A | | 3/2005 | |
| WO | WO 00/47124 | | 8/2000 | |

* cited by examiner

DEVICES AND METHODS FOR REMOVING UNWANTED TISSUE

CROSS-REFERENCE TO RELATED APPLICATIONS

This application is a National Stage Application of International Application Number PCT/US2014/061973, filed Oct. 23, 2014; which claims the priority benefit of U.S. Provisional Application Ser. No. 61/894,736, filed Oct. 23, 2013 and U.S. Provisional Application Ser. No. 61/951,205, filed Mar. 11, 2014, the disclosures of which are incorporated by reference herein in their entirety, including any figures, tables, or drawings.

BACKGROUND OF THE INVENTION

The skin of most mammals, including humans, is generally supple and has a variety of structures embedded therein, such as blood vessels, nerves, fat cells, layers, and glands. Occasionally it is necessary to remove skin or other unwanted tissue.

For example, polydactyly or the congenital presence of extra digits at birth is the most common of the duplication anomalies of congenital deformities. When humans are affected, typically this deformity involves either the hands or the feet, and can less frequently involve both the upper and lower extremities. Most cases of polydactyly are inherited, manifesting as a dominant or recurrent trait; but the condition can present sporadically in humans.

Typically, polydactyly is most common on the ulnar (post axial little finger) side of the hand and is less common on the radial (thumb) side, and is very rarely seen within the middle three digits. These are referred to as postaxial (little finger), preaxial (thumb), and central (ring, middle, index fingers) polydactyly, respectively. Polydactyly is most commonly seen as an abnormal fork in an existing digit. Polydactyly is further classified as being either Type A or Type B (radial), which describes the variable size of the digits. Extra digits can be fully formed with a correct number of joints and bones, or they can be poorly formed as rudimentary digits. Fully formed digits are classified as Type A polydactyly and poorly formed or rudimentary digits are classified as Type B polydactyly. Thus, a person with a small rudimentary digit on the outside of the little finger would be diagnosed as having postaxial polydactyly Type B.

Treatment for polydactyly is generally aimed at improving the functionality and/or appearance of the limb involved. Indirectly, treatment will simultaneously limit progression of the deformity and potentially concurrent limb dysfunction, and improves the esthetic appearance of the hands or feet of the affected patient. The Type B form of postaxial polydactyly is ten times more frequent in African Americans than in other races, occurring in 1 out of 143 African American newborns. The deformity occurs less frequently in the other races, and is also common as an associated malformation in many syndromes. This specific type of polydactyly, seen in conjunction with other syndromes, is characterized by the presence of an incompletely formed or rudimentary finger attached to the hand or foot through a thin stalk or pedicle.

The accepted "standard of care" for this type of anomaly, is to perform suture ligature or to apply a vascular clamp around the base of the extra digit. Once treated the infant's digit, whether hands or feet, are bandaged and the patient is discharged home where the polydactyl digit[s] will hopefully undergo dry necrosis and auto amputation in about 10 days.

Unfortunately, when suture ligature fails, several types of complications can result. The overall rate of complications associated with ineffective suture ligature or vascular clamps is approximately 24%, with 16% resulting in a "nubbin" and likely neuroma formation. Other complications can include trauma to the extra digit, which can be painful, hemorrhage following avulsion, venous engorgement without auto amputation, and infections.

When the residual tissue results in neuroma formation, the patient experiences a lifetime of discomfort due to the sensitivity of the lesions. Moreover, if the patient subsequently desires a curative repair of the lesion to resolve the discomfort caused by the neuroma, the procedure involves neurosurgical and cosmetic intervention that can be very costly and will likely require undergoing general anesthesia and its risks.

Another procedure, performed by a similar technique is castration of animals, particularly large bovines. One method of castration is performed by applying a ligature band around the scrotum. This technique entails placing a strong, elastic band around the scrotum of the animal, above the testis. The band constricts around the spermatic cord, testicular blood vessels and other tissues, causing atrophy of the testis and lower scrotum. If the method, sometimes referred to as "banding", is performed correctly, within a few weeks the testis and surrounding scrotum below the band will atrophy and fall off the body.

Another technique utilizes a flat-head clamp that is placed across the scrotum. The clamp can be used to apply pressure to the spermatic cords and blood vessels leading to the testicles. The application of sufficient pressure will crush these structures causing a gradual atrophy of the testicles. When done correctly, the scrotum remains intact and only the testicles will atrophy and become ineffective. If done incorrectly, gangrene can occur, the animal may not be completely castrated, or the animal can suffer unusual pain after the procedure, inhibiting growth and thriving of the animal.

Thus, the usual tools and appliances used for these techniques require careful placement to ensure successful treatment, whether it is removal of unwanted external tissue or the alteration of internal tissues.

BRIEF SUMMARY OF THE INVENTION

The subject invention provides devices and methods for treating and/or removing unwanted tissue. In particular, one embodiment of the subject invention provides devices and methods of use for intervention and treatment of Postaxial Type B polydactyly. More specifically, the devices can be used and the methods can be performed by the primary caretaker of an affected patient, in particular, during the immediate post-delivery or newborn period on an infant suffering from polydactylism. The embodiments of the subject invention can also be utilized for removal of other redundant or extraneous skin tissue, such as moles, skin tags, warts, and other skin growths.

Another embodiment of the subject invention provides devices and methods used in castration of animals. In particular, these embodiments can be useful for the castration of bovine, equine, or porcine species, or other animal species where the scrotum is easily accessible and internal structures of the scrotum are externally discernable. The devices and procedures include the use of novel hemostatic clamps according to the subject invention. In one embodiment, the clamp employs at least two opposing surfaces to apply pressure to tissue, so that the tissue is crimped or fused together. For treatment of polydactyly, the clamp can be placed at the base of the digit. The application of sufficient force by the clamp causes the tissue at the opposing faces to fuse together. After application of the clamp for an appropriate time, a sharp implement, such as, for example, a scalpel or surgical-grade razor can be used to amputate the tissue or digit. Advantageously, when the clamp is removed, the fused tissue prevents bleeding at the amputation site and encourages withdrawal of any residual nerves from the area of the amputation. The design of the clamp allows it to be smaller and more compact than typical clamps, making it more practical for use with smaller tissues and infants.

In another embodiment, the clamp includes dual slots positioned on either side of a mortis and tenon configuration formed in the two opposing surfaces. For performing castration, the blood vessels in the scrotum can be aligned within the slots and the spermatocord and other blood vessels to the testes placed between the dual slots, so that they are aligned between the mortis and tenon. When the clamp is closed, the tissues in-line with the mortis and tenon are pushed by the tenon on one surface into the mortis formed in the other surface, where they are compressed to the point of being crushed, causing incapacitation of the testis. The blood vessels aligned within the slots are protected from the opposing surfaces and the mortis and tenon, so that they can continue to supply the scrotum with some blood flow. After the procedure, the testis will eventually atrophy and be absorbed by the body, leaving the scrotum smaller, but intact.

Certain clamp embodiments of the subject invention can assist the clinician in achieving a fast and curative removal of unwanted or redundant tissue, such as rudimentary digits. Other embodiments can be used to incapacitate the testes of an animal. The procedures can be performed in a relatively painless and aseptic fashion and, once complete, a painless and suture free permanent removal of the digit or atrophy of the testes is achieved. The polydactyly patient can then leave the hospital or office with a permanent repair and with an esthetically pleasing appearance. Likewise, a castrated animal can be released without concern for infection or gangrene of the scrotum, since there is no open wound.

BRIEF DESCRIPTION OF THE DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale; furthermore any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which.

DETAILED DISCLOSURE

Figure 1:
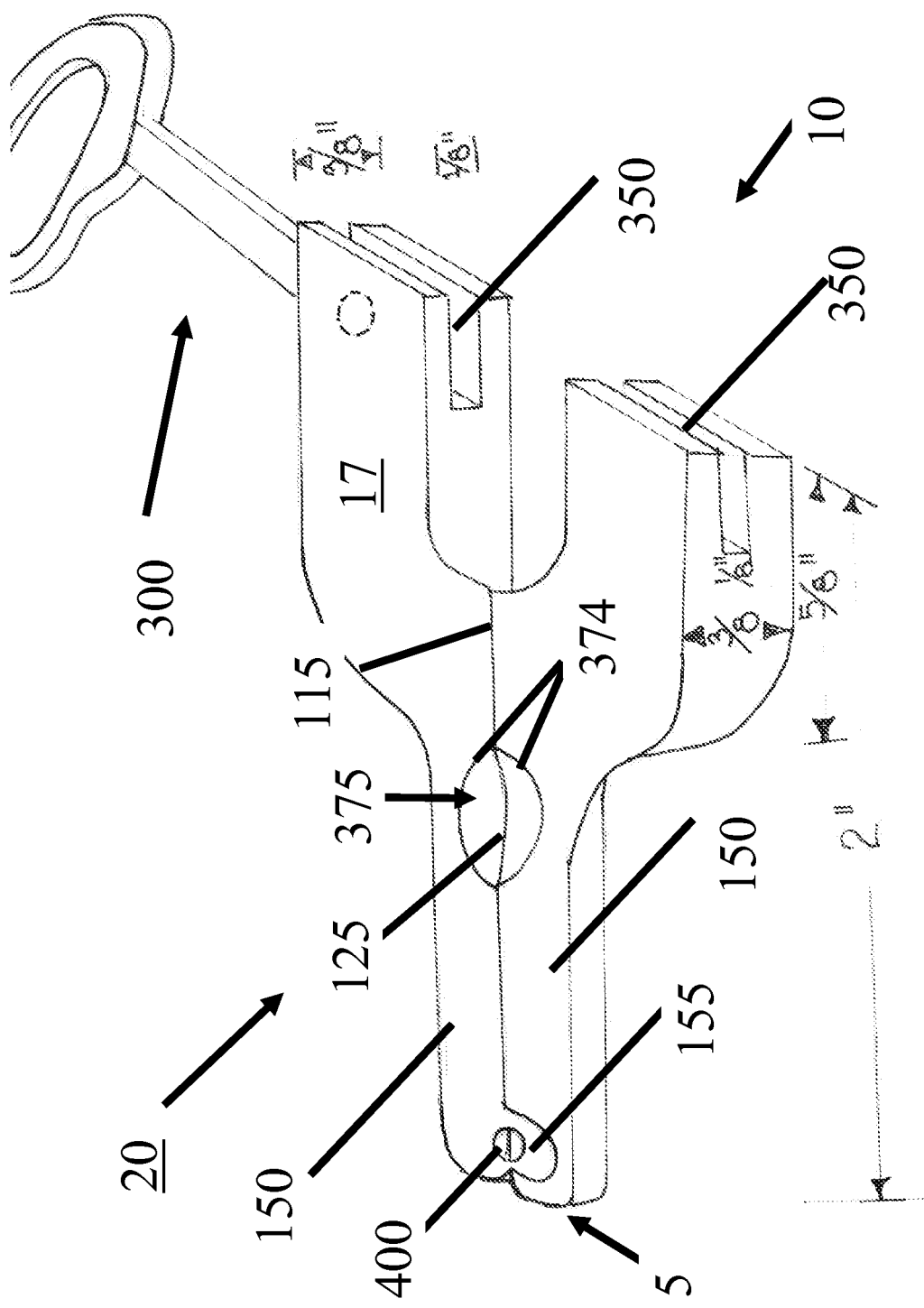
FIG. 1 is an illustration of a perspective view of one embodiment of the clamp of the subject invention.

The subject invention provides tissue clamps and methods of use. More specifically, the subject invention provides embodiments of externally applied hemostatic and castration clamps, or similar devices, capable of being used to remove tissue from the exterior of the body or affect tissues within the body. The devices and methods of the subject invention are particularly amenable for crushing, crimping, or fusing tissues, which can be useful in treating polydactylism and are particularly beneficial for use on infants The embodiments of the subject invention can also be used to remove redundant or extraneous skin tissue in adults, such as, for example, skin tags, moles, or warts. An alternative embodiment has specific structural features that allow it to be used for performing castration, particularly on large animals. Advantageously, the devices and methods of the subject invention can provide a less painful, quicker, and effective treatment, with minimal or no scarring or complications.

The embodiments of the subject invention provide tissue clamp devices for performing procedures that have previously necessitated creating open wounds in the body. The devices are relatively easy to use, minimize or prevent blood loss, provide a more aesthetic appearance to the treated tissues. A hemostatic clamp of the subject invention can provide a quick and easy method for treating polydactylism or removing unwanted tissue from the surface of the skin. A castration clamp, operated in a similar fashion, can provide a quick, more sanitary method for castrating field animals and can minimize stress on the animal.

The novel, and relatively simple, devices and procedures of the subject invention are preferable to the suture ligature or vascular clamp methods used currently around the world, for both of these procedures. These clamps and method of use described herein eliminate most, if not all, of the complications too frequently associated with the suture method, and should appeal to the clinicians involved in performing these procedures. The approach using the clamp and method of the subject invention reduces the time required to achieve a curative end, and achieves a more rapid and esthetically pleasing result without the shortcomings associated with the ligature approaches. The cost of both of these procedures can be low. Treatment of polydactylism with the clamp embodiments of the subject invention poses significantly less risk to the patient when compared to a neuroma repair. Similarly, castration, performed with alternative embodiments of the clamp of the subject invention, can be more accurate, quick, and, reduce risk of infection or gangrene.

The embodiments of the subject invention are particularly useful for treating polydactylism and alternative embodiments are effective for performing castration; however, a person with skill in the art will recognize other uses for the devices and methods of the subject invention. For example, other tissues external to the body, such as, for example, moles, skin tags, hemorrhoidal tissue, raised scar tissue, warts, and cancerous and non-cancerous tumors, can also be excised by the devices and methods of the subject invention. Wound care and closure can also be performed with the embodiments of the subject invention.

Thus, while the subject application describes, and many of the terms used herein relate to, a use for treatment of polydactylism or castration, modifications for other uses will be apparent to a person with skill in the art having benefit of the subject disclosure.

In the description that follows, a number of terms relating to the removal of external tissue or polydactyl digits and castration are utilized. In order to provide a clear and consistent understanding of the specification and claims, including the scope to be given such terms, the following definitions are provided.

The term "patient" as used herein, describes an animal, including mammals to which the systems and methods of the present invention can be applied. This includes mammalian species that can benefit from the disclosed systems and methods including, but not limited to, apes, chimpanzees, orangutans, humans, monkeys; domesticated animals (e.g., pets) such as dogs, cats, guinea pigs, hamsters, and rabbits. Veterinary uses are also contemplated for the subject invention, and include uses for large or small animals such as, for example, cattle, buffalo, bison, horses, donkeys, swine, sheep, goats; various types of farm birds; exotic animals typically found in zoos, such as bears, lions, tigers, panthers, elephants, hippopotami, rhinoceroses, giraffes, antelopes, sloths, gazelles, zebras, wildebeests, prairie dogs, koala bears, kangaroos, opossums, raccoons, ostriches, pandas, hyenas, seals, sea lions, elephant seals, otters, porpoises, dolphins, and whales. Furthermore, human or non-human animal patients can range in age from neonates to elderly.

The term "clinician" as used in the subject invention is merely for literary convenience. The term should not be construed as limiting in any way. The devices, apparatuses, methods, techniques and/or procedures of the subject invention can be utilized by any person desiring or needing to do so and having an understanding of the invention.

In addition, the terms "clamp" or "tissue clamp" are used interchangeably to refer to either a hemostatic clamp or a castration clamp of the subject invention.

Also, as used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct, or indirect, physical or remote.

Finally, reference is made throughout the application to the "proximal end" and the "distal end." As used herein, the proximal end is that end of a clamp embodiment around which the arms of the clamp pivot. Conversely, the distal end of the device is that end at which the arms of the clamp separate or open.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached figures on which the same reference numerals are used throughout to indicate the same or similar components. With reference to the attached figures, which show certain embodiments of the subject invention, it can be seen that a tissue clamp 20 of the subject invention generally comprises two arms 150 operably connected at their proximal ends 5. When the arms are pivoted laterally, i.e., away from each other, there is provided an opening 110 at the distal end 10 leading into the mouth 115 of the clamp, into which a tissue 25 can be inserted, so that a part thereof can be constricted or compressed between opposing faces 125 on each arm. When the arms are pivoted together and/or towards a medial line 15, the opposing faces are juxtaposed and any tissue therebetween is constricted or crushed. To ensure that the arms 150 provide sufficient constriction force and they remain juxtaposed until such time that they are to be removed from the tissue at least one locking mechanism 300 can be operably connected to each arm to maintain the medial position of the arms or juxtaposition of the opposing faces. Particular embodiments further include a scalpel or blade incorporated or built-into a tissue clamp, which can be used to cut away excess or extraneous tissue that is not between the juxtaposed opposing faces.

The hemostatic clamp embodiments, used for tissue fusion, can include the above-listed features and can further include a divit 375 where the opposing faces have narrower width (W), such that they form a shallow depression in the front surface 17 of the clamp when the arms are brought together. Each arm can have a depression 374 that align when the arms are brought together to form a divit. When tissue is excised, the divit allows for a scalpel, razor blade, or other appropriate sharp blade to be placed as close as possible to the body. This can create a smaller area of crimped or fused tissue or, as will be discussed below, a smaller skin tab 27.

Figure 31:
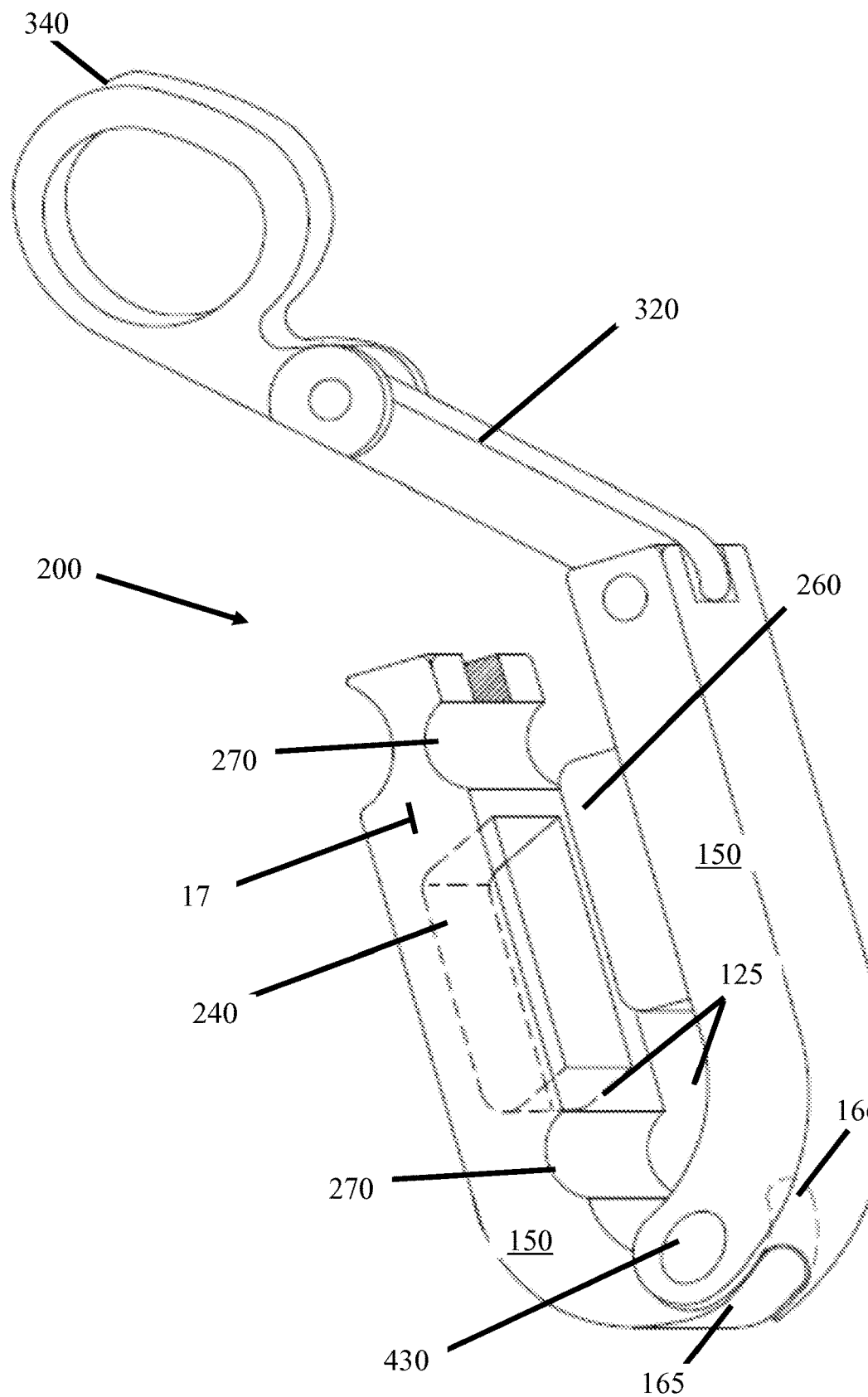
FIG. 31 illustrates one embodiment of a castration clamp according to the subject invention.
Figures 32, 33:
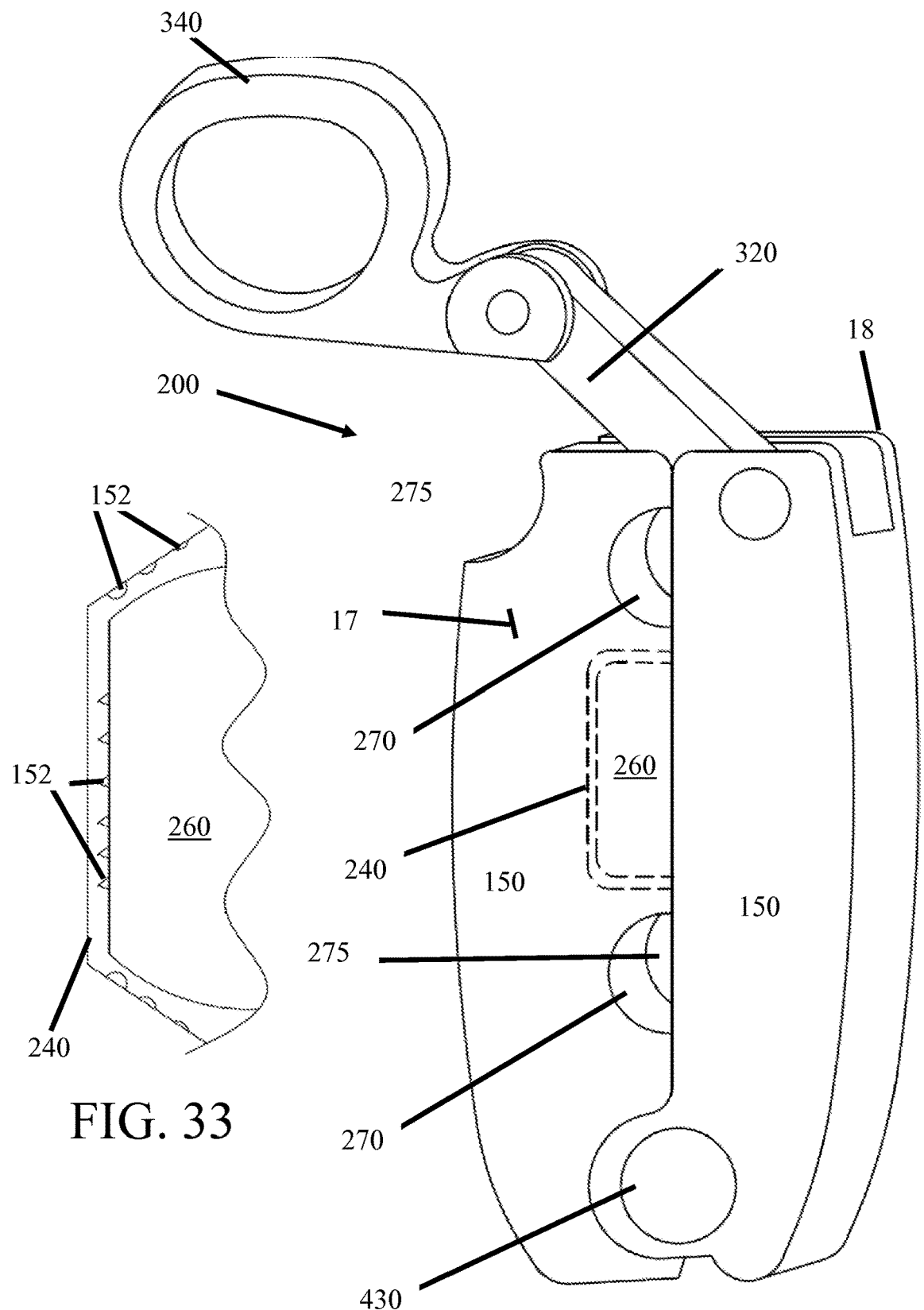
FIG. 32 illustrates another embodiment of a castration clamp according to the subject invention.
FIG. 33 illustrates an alternative embodiment of a mortis and tenon configuration.

A castration clamp 200 embodiment of the subject invention can include the general components described above and can further include at least two notches 270 that form at least two channels 275 when the opposing faces 125 are brought together. There can also be included a mortis 240 cut into the one opposing face and a tenon 260 extending out from another opposing face, such that when the opposing faces are brought together the tenon fits into the mortis. Tissue placed between these two components will be forced by the tenon into the mortis and constricted or crushed. Advantageously, the use of the mortor and tenon allows for the application of greater pressure to the tissues without an increase in force being applied to the clamp. FIGS. 31 and 32 illustrate embodiments of a castration clamp.

In general, a hemostatic clamp and a castration clamp of the subject invention have similar components that allow them to operate in a similar fashion. The differences between a hemostatic clamp and a castration clamp can be most evident in the construction and/or configuration of the faces on the arms, which will be described in detail below. Thus, while the subject application and the descriptions herein of a tissue clamp are directed particularly to a hemostatic clamp, it should be understood that the descriptions can be equally applicable to embodiments of a castration clamp. Where there are specific differences in components between a hemostatic clamp and a castration clamp, the subject application will set forth these differences.

With regard to the body of a tissue clamp 20, the materials utilized can depend upon whether the clamp is intended to be disposable for single use or sterilized for repeated use. It can also be preferable for the clamp to be made of one or more biocompatible materials. In a specific embodiment, at least the arm faces 125 that come into intimate contact with tissue comprise a biocompatible material. In a further embodiment, at least the arm faces are disposable.

The materials that can be utilized for disposable medical devices are known to those with skill in the art and can include, but are not limited to, plastics, nylon, metals, glass, ceramics, or combinations or composites thereof. Ideally, the material utilized, at least for the arm faces, will have sufficient rigidity that an appropriate amount of force can be applied to achieve proper fusing of the tissues. The materials utilized for sterilizable devices are also, preferably, one or more non-reactive and/or biocompatible materials. Such materials are known to those with skill in the art and can include, but are not limited to, various types of metals, metal alloys, plastics, ceramics, naturally-derived products, or combinations thereof. More specific examples include, but are not limited to, titanium, cobalt-chromium-molybdenum alloys, steel, titanium-carbide-coated stainless steel, nylons, polyethylenes, combinations or composites thereof.

Ideally, the one or more materials selected for a reusable device are capable of withstanding repeated sterilization procedures. Further, the material utilized, at least for the arm faces, will ideally have sufficient rigidity that an appropriate amount of force can be applied to achieve proper fusing of the tissues. The selection of an appropriate non-reactive and/or biocompatible disposable or reusable material is within the competence of those skilled in the art. In addition, one or more parts of the clamp can be coated or covered with one or more pharmaceuticals. For example, the arms of the clamps, or at least the arm faces can be coated with a silver nitrate or other silver salt. Anesthetics can also be used on a clamp, as well as other chemicals or compounds, such as those to control bleeding if it occurs, prevent infection, or inhibit scarring. It is within the skill of a person trained in the art to determine any number of coatings that can be used with the embodiments of the subject invention. Such variations are within the scope of this invention.

Figure 4:
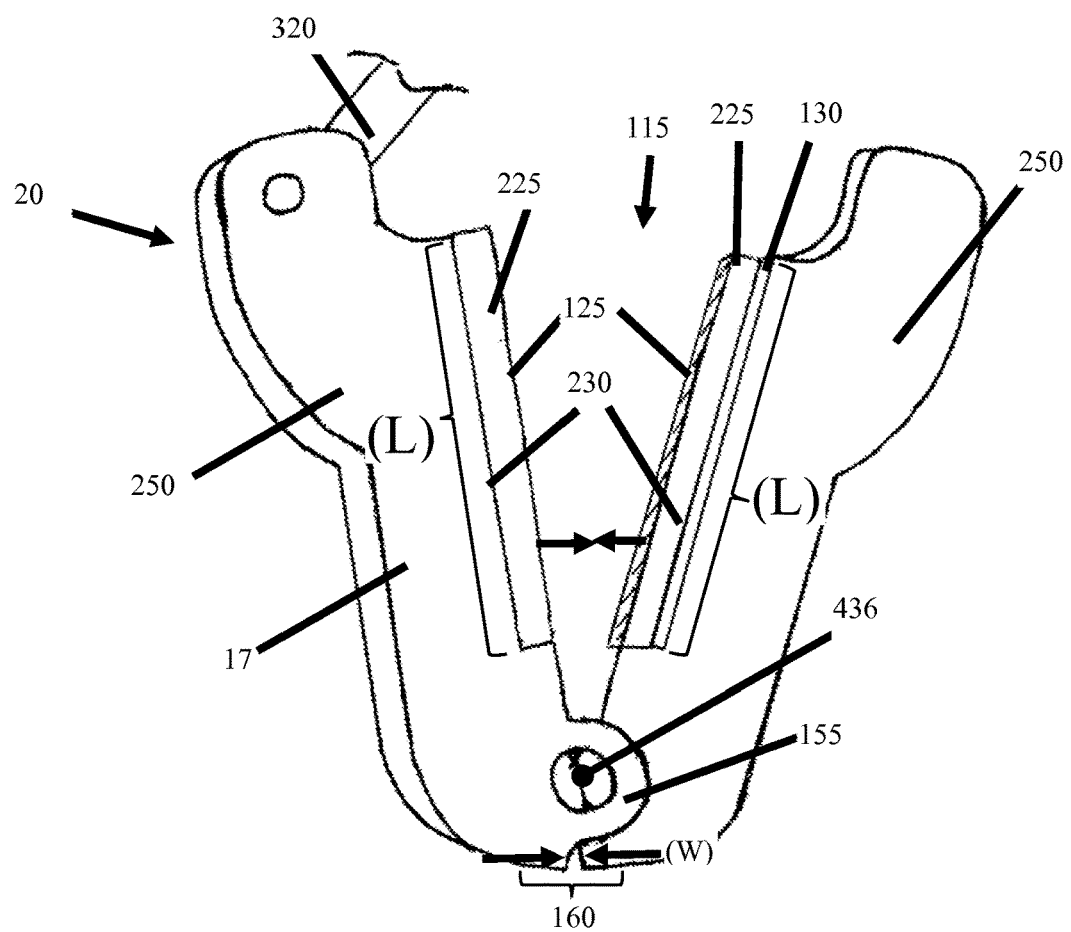
FIG. 4 shows an alternative clamp embodiment of the subject invention.

With regard to the arms of a clamp 20, it can be seen in FIGS. 1 and 4 that the faces of the clamp are supported by the arms. Thus, the alignment of the arms 150 can affect the juxtaposition of the faces 125. In one embodiment, the arms are rotatably joined at or about their proximal ends. In a further embodiment, the arms are joined with any of a variety of rotation mechanisms 400, such as, but not limited to, a pin, bolt, rod, screw, or other similar device that maintains their alignment, while allowing them to rotate. There can also be used press-fit mechanisms, such as, for example, press-fit bolts or pins. Ideally, the rotation mechanism has minimal or no surface features on the bearing head 410, which can, when present, provide areas for harboring bacteria or other undesirable organisms or material. In addition, there can be one or more spring or spring-like mechanisms incorporated with the rotation mechanism or that operate the rotation mechanism to cause the arms to be biased, so that the opposing faces are held apart unless forcibly brought together or juxtaposed with each other.

Figure 2A:
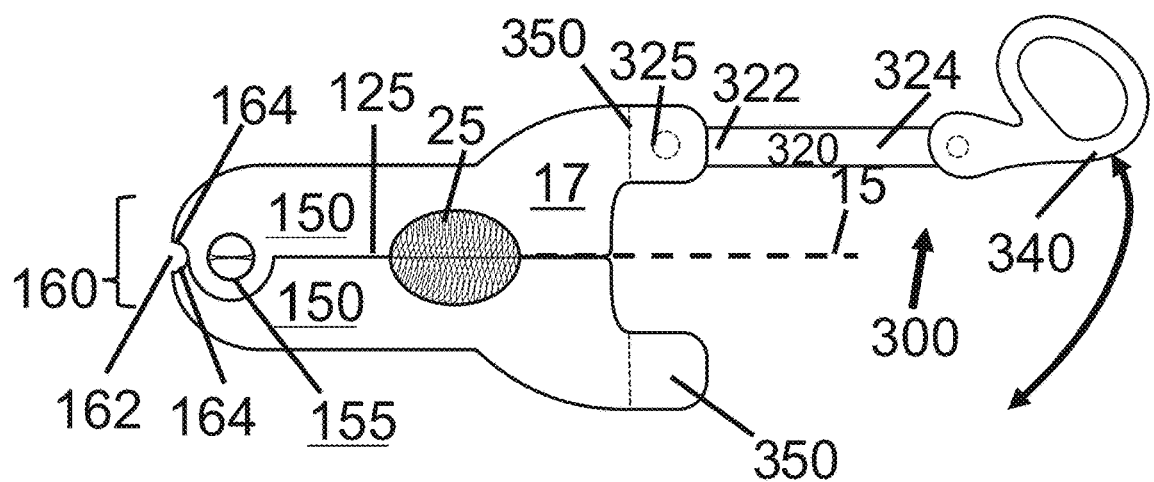
FIG. 2A is a drawing of a top plan view of one embodiment of the clamp of the subject invention.
Figure 2B:
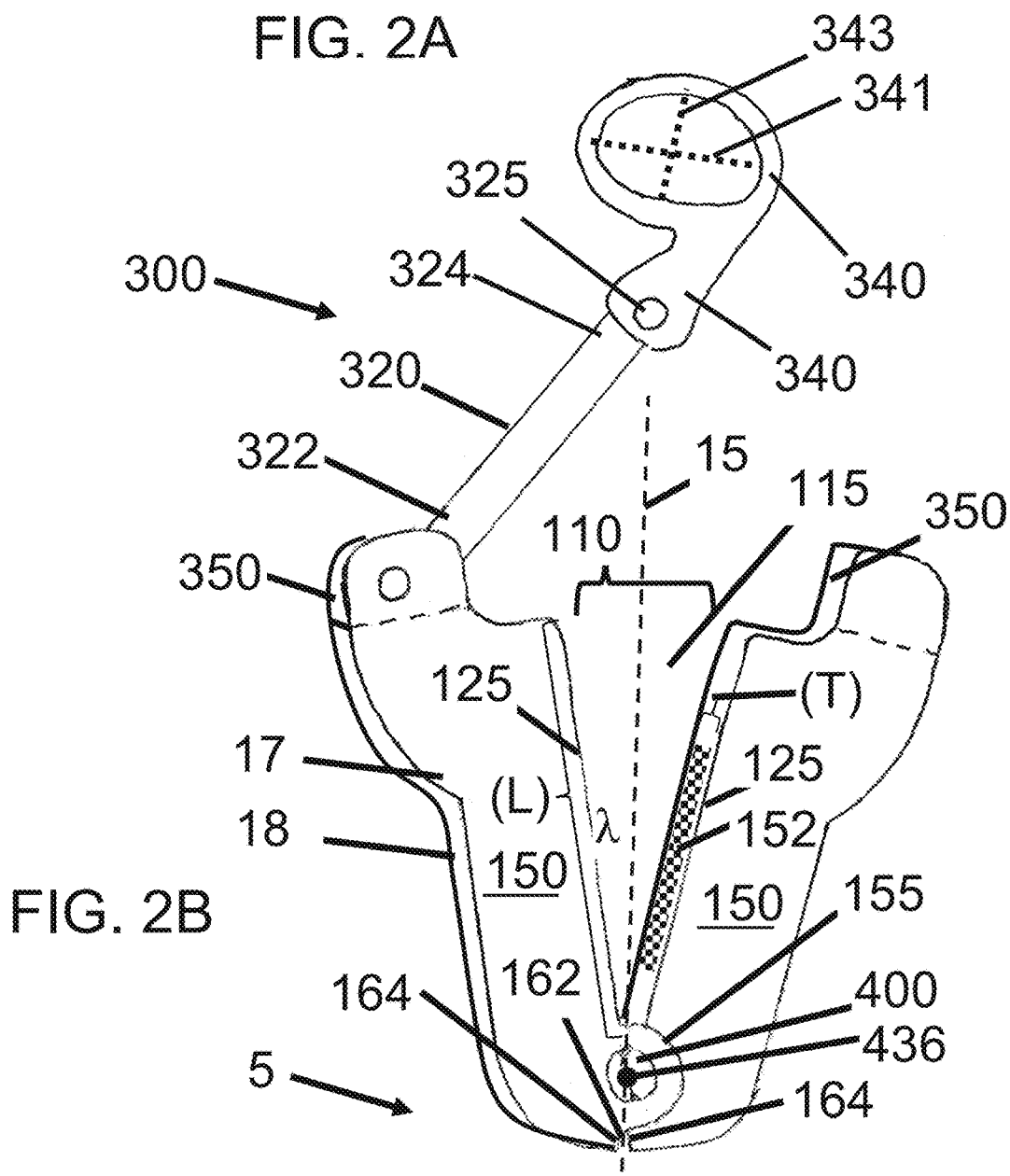
FIG. 2B is a drawing of a top plan view of an embodiment of a clamp, according to the subject invention, with the arms separated.
Figure 15:
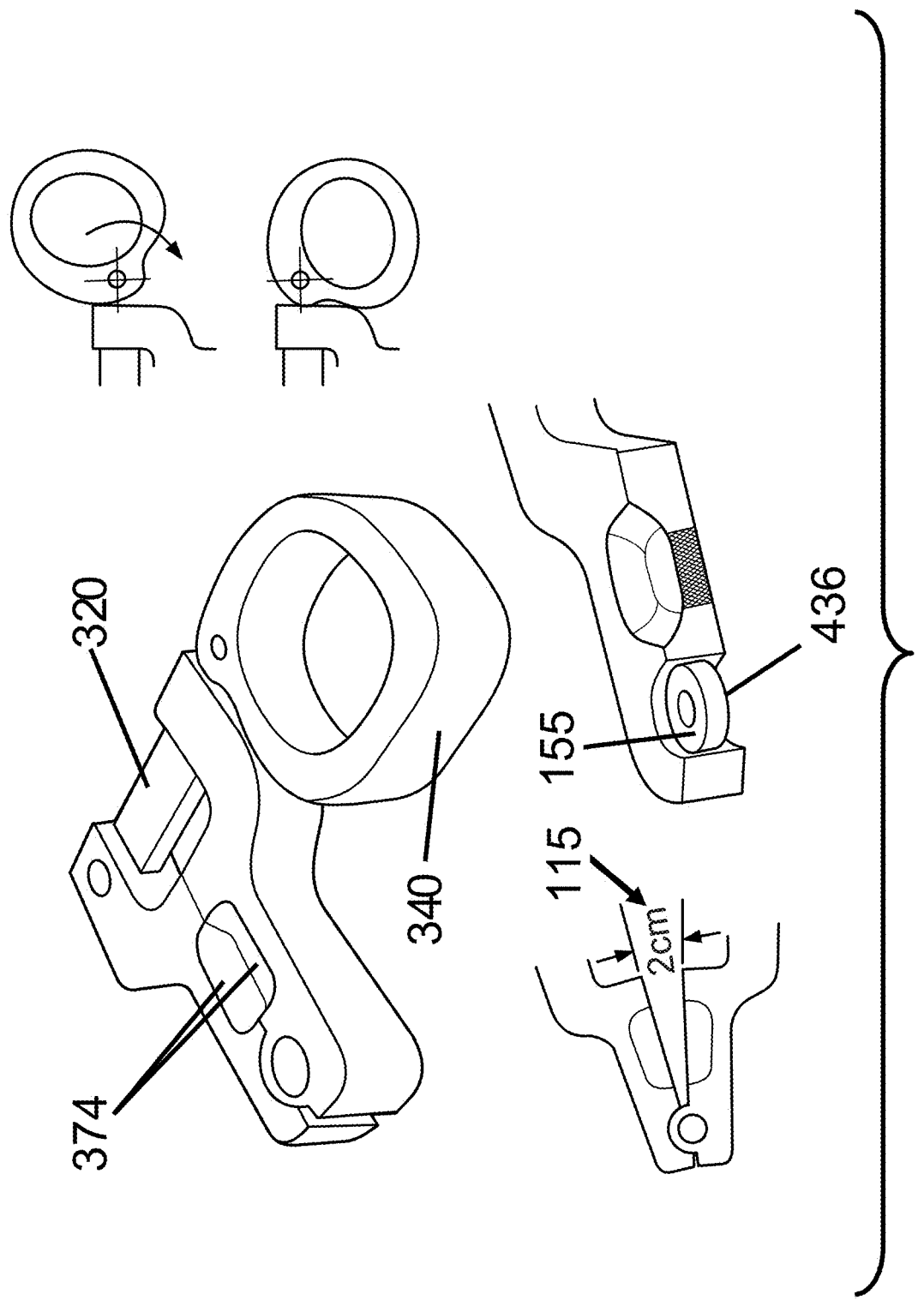
FIG. 15 illustrates further embodiments of toggle spindles and divits that can be used with the tissue clamp embodiments of the subject invention.
Figure 16A:
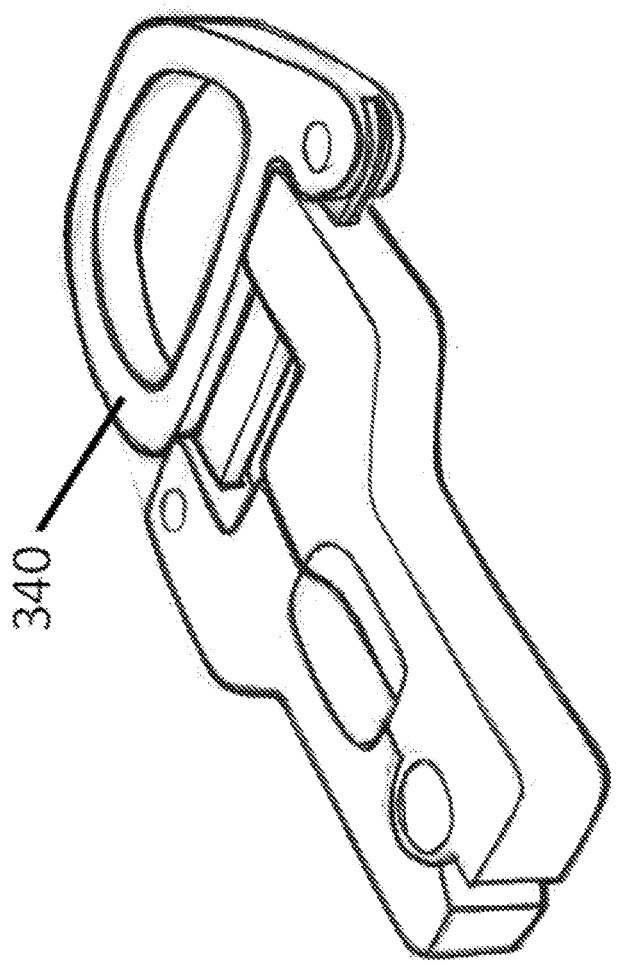
FIGS. 16A and 16B illustrate another alternative embodiment of a toggle spindle and divit that can be used with the tissue clamp embodiments of the subject invention.
Figure 16B:
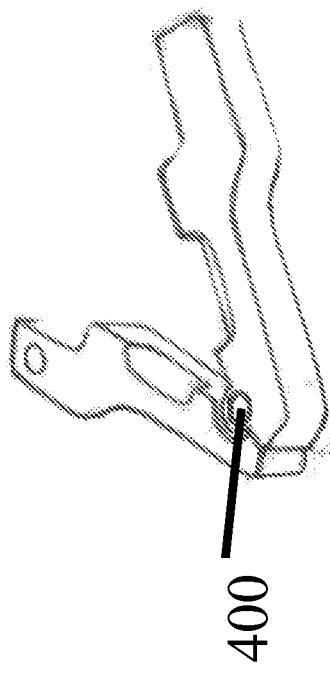
Figure 17:
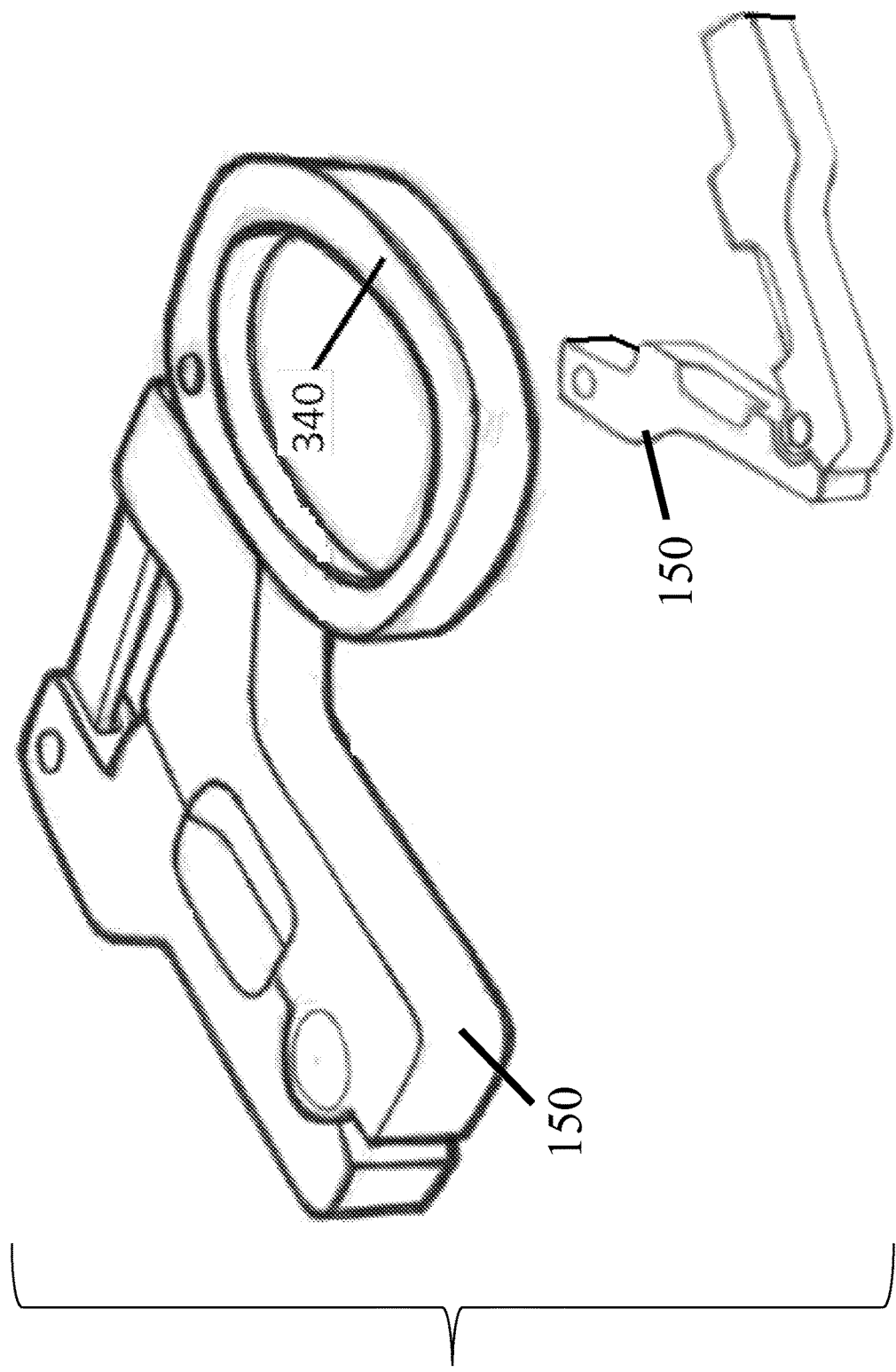
FIG. 17 is a perspective view of another embodiment of the invention in a closed position and an open position.

In a further embodiment, there can be flanges 155 on one or both of the arms that aid in aligning the arms and can also aid in maintaining the alignment of the arms. FIGS. 2A and 2B illustrate an embodiment where a first arm has at least one flange 155 that overlaps the front surface 17 or rear surface 18 of the second arm and is secured with a rotation mechanism 400 that provides a pivot axis 436. FIG. 15 illustrates an embodiment where one arm has a single flange 155 and the other arm has two flanges. The single flange on the one arm can be sandwiched between the two flanges on the other arm. When assembled the flanges sandwich together and they can be secured, so that they can pivot relative to each other along the same pivot axis 436.

FIG. 2B illustrates an embodiment in which the arms pivot at or about their proximal ends 5 to form an opening 110 leading to a mouth 115 of the tissue clamp between the arms, into which a tissue can be inserted. In one embodiment, the arms can swing freely apart, such that the angle λ forming the mouth can range from 0° (the arms and faces 125 completely juxtaposed) to approximately 180° (the arms substantially linearly aligned). More specifically, embodiments of the subject invention can have a mouth opening that forms an angle of at least 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, 185°, and/or an angle in a range between any two of the listed values. In a particular embodiment, the mouth 115 can open to an angle between approximately 15° and approximately 20°. In a more specific embodiment, the mouth can open to an angle of approximately 17°. This can provide an opening at the distal end 10 that is approximately 2 cm in width, as illustrated, for example, in FIG. 15. However, a larger λ can be advantageous when utilizing the device on larger tissues. The angle can also be greater than 185°.

Figure 9:
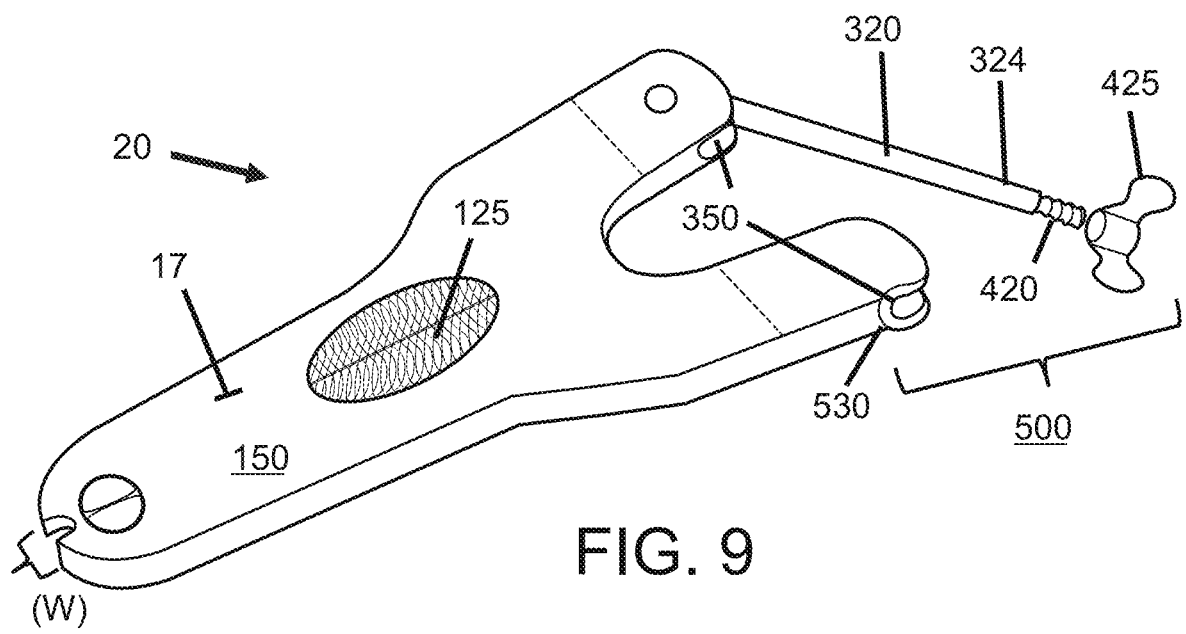
FIG. 9 illustrates an alternative embodiment of a clamp, according to the subject invention, where the locking mechanism is a nut and bolt configuration.

In an alternative embodiment, one or more mechanical joint stops 160 can be used to limit the rotation, thus the λ, of the mouth 115. In one embodiment, the proximal end 5 of at least one arm is configured with a joint stop to restrict the rotation of the arms and λ of the mouth 115. The embodiments shown in FIGS. 1, 2A, and 2B utilize an abutment-type joint stop, where the configuration of the arms provides interference against the arm openings beyond a certain angle. In one embodiment, a joint stop comprises a cut-out 162 between the proximal end 5 of the arms, whose width (W) dictates the range of motion of the arms. FIG. 9 demonstrates an example of the width (W) of a cut-out 162. With this embodiment, the proximal ends of the arms can rotate through the width of the cut-out. At the extremes of rotation, the opposing sides 164 of the cut-out will abut each other, preventing the arms from rotating any further, thus restricting the angle of the mouth.

FIG. 31 illustrates an alternative embodiment of a joint stop having a tongue 165 on one arm that fits into a groove 166 in the opposite arm. The length of the tongue and the groove it rotates into can dictate how far the arms can rotate. A joint stop 160 can also be incorporated into the rotation mechanism 400 and/or one or more flanges 155 on an arm. Mechanical joint stops are well-known in the art. Such variations, which provide the same function, in substantially the same way, with substantially the same result, are within the scope of the subject invention.

Figure 5:
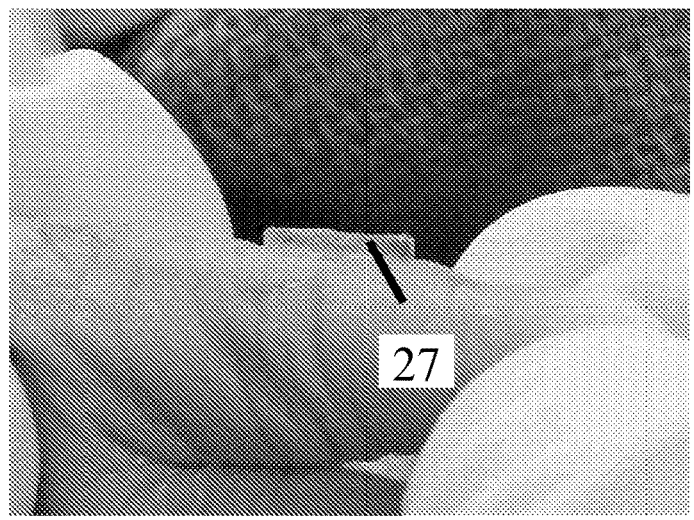
FIG. 5 shows a fused tissue tag formed on the surface of the remaining digit, by a clamp of the subject invention.
Figure 6:
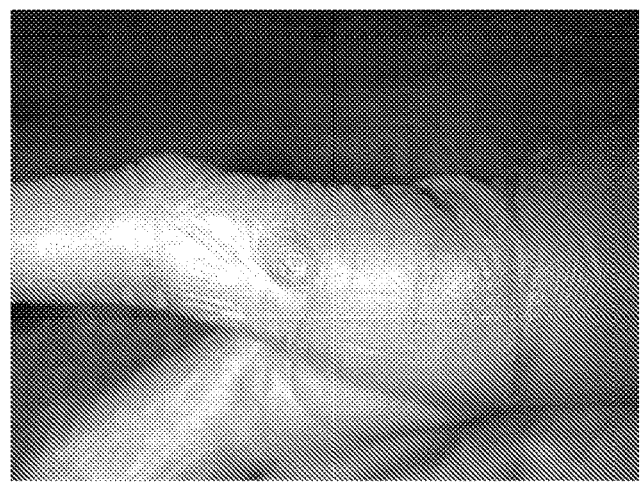
FIG. 6 shows a scarred region on the post-axial area of the hand caused by removal of a postaxial polydactyl digit by a suture ligation technique.
Figure 7A:
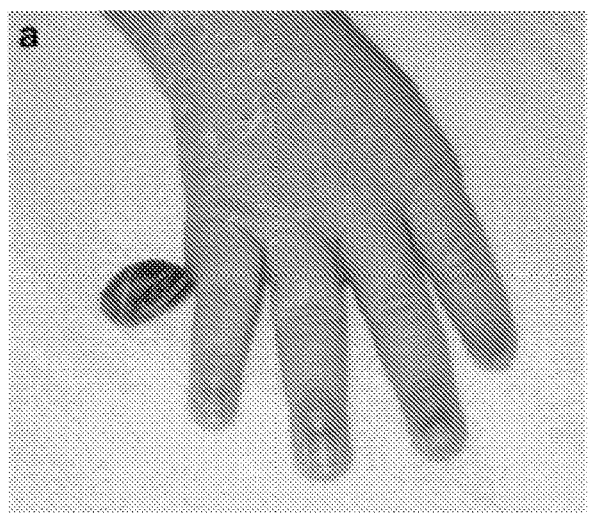
FIGS. 7A and 7B show examples of neuromas formed due to ineffective suture ligation.
Figure 7B:
Figure 8A:
FIGS. 8A and 8B are photographs of an infant at birth exhibiting polydactylism (FIG. 8A) and at 6 months of age (FIG. 8B) after treatment with a clamp of the subject invention.
Figure 8B:

It can be seen in the embodiment in FIG. 1 that, when juxtaposed, the faces 125 on each arm are substantially aligned. The juxtaposition of the faces is important, so that pressure exerted on a tissue therebetween effects fusion of the tissue and creates a sealed skin tab 27 that inhibits bleeding, an example of which is shown in FIG. 5. In one embodiment, the faces 125 are mirror images of each other, such that when they come together, or are juxtaposed, they align along all or most of their lengths (L). FIGS. 2B and 4 illustrate examples of this wherein the faces are substantially identical mirror images that can align along most or all of their entire length (L), that is, from the proximal end 5 to the distal end 10, when juxtaposed.

In an alternative embodiment, the faces are not mirror images, but, rather, one face can be a different shape than the other. For example, one face can have a greater surface area than the opposing face. This can be advantageous for clamps that may become misaligned due to age or repeated use, because the smaller area face will be able to exert force against the larger area face, even if the arms become misaligned, bent or are otherwise not exactly lined up.

The length of a face, that is, the distance from the proximal end 5 to the distal end 10, can vary and may depend upon a variety of factors understood by a person with skill in the art and having benefit of the subject disclosure. In one embodiment, the length of at least one face 125 is equal to, or approximately equal to, the length of the mouth 115, as shown, for example, in FIG. 2B. Alternatively, the length of at least one face is less than the length of the mouth, as shown, for example, in FIGS. 1 and 4. With this embodiment, the faces on each arm are located within the mouth, and distanced from the distal end 10 of the arm, so that they are closer to the proximal end 5. In the specific embodiment, shown in FIG. 1, the faces are approximately central to the mouth. In another specific embodiment, the mouth is closer to the proximal end 5, which is illustrated, by way of example, in FIGS. 11A-11C, where the mouth is closer to pivot axis 436.

Figure 12A:
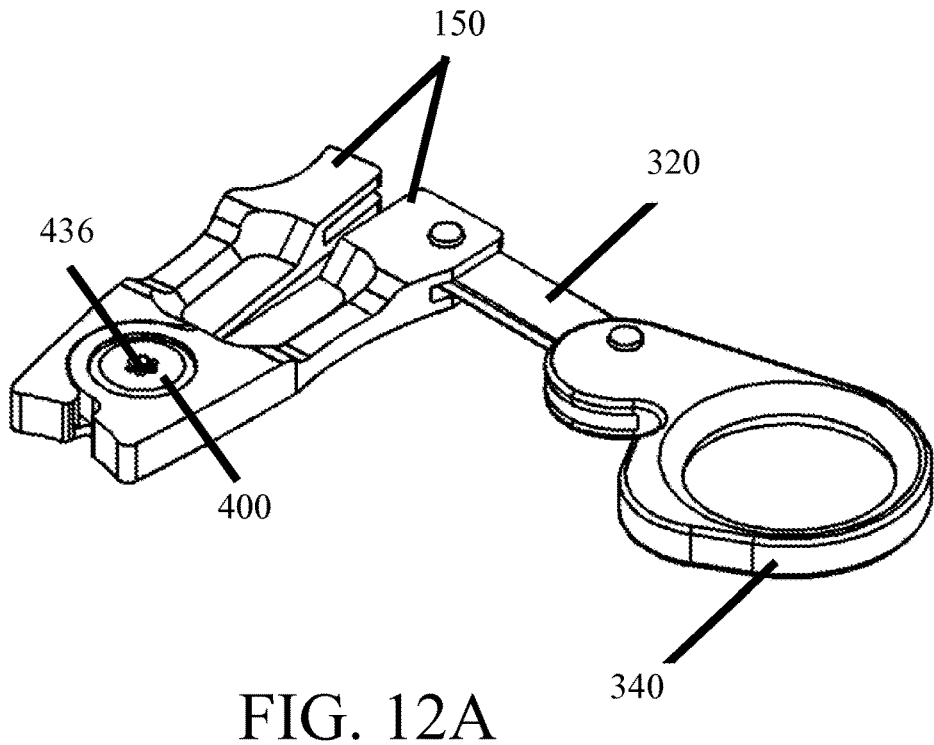
FIG. 12A is a perspective view of the front surface of another alternative embodiment, shown with a toggle arm removed from the longitudinal slot.
Figure 12B:
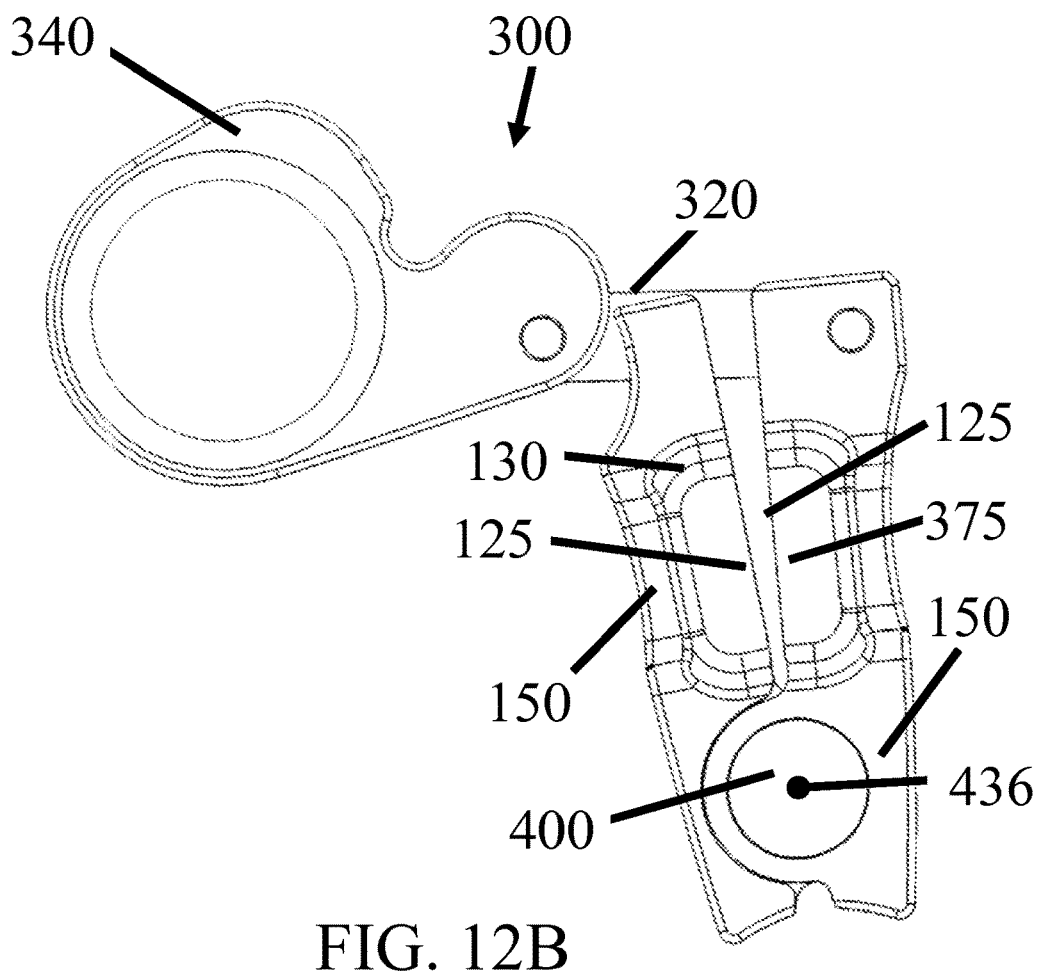
FIG. 12B is a front surface view of the embodiment shown in FIG. 12A, with the toggle arm in the longitudinal slots.

With the hemostatic clamp 20 embodiments shown in FIGS. 1, 2A and 2B, the arms and associated faces thereon are configured as single unit pieces. Thus, an arm and a face can comprise the same material or a homogeneous mixture of two or more materials. Further, with this embodiment, the arm and face can be inseparable. Alternatively, the arm and face can comprise different materials. The different materials can transition from component, an arm, to another component, the face. For example, the arm may comprise one type of material and the face can comprise another type of material, with a material transition zone 130 therebetween. FIGS. 4 and 12B illustrate non-limiting examples of transition zones 130. This allows, for example, the face to comprise a more rigid material or a material otherwise better able to withstand the forces applied to the tissue. Likewise, the arm can comprise a material better suited for being handled or one that allows for better ergonomic shapes or has some other characteristic making it desirable for the arm. With this embodiment, the arm and face can be a single, inseparable component.

Alternatively, FIG. 4 illustrates an embodiment wherein the arm and the face are configured as two different components that can be fitted together. With this embodiment, a face component 225 can be a piece that couples with an arm component 250. This can allow the face component to be made of one material and the arm component to comprise a different material. This can be advantageous because it allows the face component to be manufactured of a more rigid, specialized, or even more expensive material and the arm component to be manufactured from a less rigid or less expensive material.

In one embodiment, the face component 225 can be configured as a plate, as seen in the example in FIG. 4. The arm component can include a slot 230 for receiving and operably connecting the face component, as indicated in FIG. 4. The plate can be made of such materials as titanium, cobalt-chromium-molybdenum alloys, steel, titanium-carbide-coated steel. These materials are very rigid, biocompatible, and well-known in the medical arts. However, they can be expensive to obtain or use. Thus, manufacturing an entire hemostatic clamp from such materials can be cost prohibitive. However, in one embodiment, the arm is manufactured from a relatively inexpensive, but FDA approved GRAS (Generally Regarded As Safe) material while a component having the face is manufactured from a more preferred material.

A further advantage with this embodiment is that it allows the hemostatic clamp to be modular. With a modular design, the face component can be replaced when necessary without having to replace the arm component as well. This can also allow different types of faces to be used, as will be explained below. Modular designs in which a smaller component of a larger device can be replaced are known to those with skill in the art. It would be within the skill of a person trained in the art to determine a device and methods by which a face component could be modularly fitted or coupled to an arm component.

Embodiments of a hemostatic clamp are particularly advantageous when the dimensions are kept as small as possible. The locations on the body in which the clamp can be used may not allow for the most appropriate placement if the dimensions of the hemostatic clamp are too large. For example, when used to remove tissue tags, which commonly appear in the creases of the body, a hemostatic clamp of smaller dimensions would be more useful.

In one embodiment, a hemostatic clamp utilizes two arms having a thickness (T), between the front surface 17 and the rear surface 18, of between approximately $\frac{1}{10}$ inch and approximately $\frac{1}{2}$ inch. In a more specific embodiment, a hemostatic clamp utilizes two arms having a thickness (T), that is, the distance between the front surface 17 and the rear surface 18, of between approximately $\frac{1}{10}$ inch and approximately $\frac{1}{4}$ inch. The overall width (W) of the device, meaning the distance across the front and/or the rear surface, can be between approximately 0.75 inch to approximately 2.0 inches. In addition, the overall length of the device, from the proximal end 5 to the distal end 10, can be between approximately 1.0 inches and 2.5 inches.

A specific embodiment of the hemostatic clamp utilizes two arms having a maximum thickness (T), between the front surface 17 and the rear surface 18, of approximately $\frac{3}{16}$ inch. The thickness of the clamp where the faces contact the skin to be fused can be approximately $\frac{2}{16}$ inch. In further specific embodiment, the overall width (W) of the device can be approximately $1\frac{1}{4}$ inches. A still further specific embodiment has an overall length (L), from the proximal end to the distal end, of approximately 2 inches.

Typically, each face 125 of the arms of the tissue clamp is a flat surface. When the arms are juxtaposed against a tissue, the force applied to the tissue by the flat faces causes the tissue to essentially fuse together between where it is contacted by the faces. There can also be extended surface features 152 on a face that can aid in creating a crimp or fused tissue area. For example, one or both faces 125 of a hemostatic clamp can have multiple ridges, nibs or similar structures thereon that press into the skin at the same time that the face is pressing against the skin.

An alternative embodiment of a tissue clamp of the subject invention can be employed to perform a safer, more effective, and less invasive castration procedure. This procedure is particularly amenable for use on large animals, where such procedures are often conducted in less than sanitary conditions. This alternative embodiment can operate similarly to a hemostatic clamp, and requires only a modification to one or both faces 125 in order to operate as a castration clamp 200.

In one embodiment, the face 125 of one arm 150 of a castration clamp has an elongated furrow or mortis 240 cut therein. The opposing arm face can have a tenon 260 formed thereon having a shape that allows it to fit into the mortis when the faces are juxtaposed, as described above for a hemostatic clamp. Tissues aligned between the mortis and the tenon will be forced into the mortis by the tenon, causing the tissues to be crushed. While some of the tissue could also be fused or crimped, as described above, the general purpose of a castration clamp is to crush or contuse the tissue to the point where it no longer functions. When performed on the ducts and blood vessels leading from, or to, the testes, it can permanently disrupt part of the ducts or blood vessels. This can render the testes ineffective and prone to atrophy.

FIGS. 31 and 32 illustrate an embodiment having a mortis and tenon with similar complementary shapes. However, it is not required that the mortis and tenon have the same or similar shape. As long as the tenon is able to fit within the mortis sufficiently to crush a tissue or tissues therebetween, the shapes of these components can vary. Extended surface features 152 have also been discussed above and can also be used with a mortis and tenon. FIG. 33 illustrates a non-limiting example of a mortis and tenon configuration where the mortis and tenon have dissimilar shapes and each has different types of extended surfaces features.

A castration clamp embodiment of the subject invention is particularly efficacious because it eliminates or inhibits the creation of an open wound in the scrotum and allows the testes to atrophy without causing extensive or long-lasting harm to the scrotum. To maintain the health of the scrotum, even as the testes atrophy within, it can be beneficial to protect at least the blood vessels that nourish the scrotal tissue. Thus, while the castration clamp is used to crush or contuse some tissue, there are other tissues that would preferably remain unaffected.

To facilitate protection of these non-target blood vessels and tissues, the castration clamp 200 can have one or more notches 270 cut within one or both faces 125 in which the non-target tissues can be positioned during a procedure to protect them from being crushed. When the arms are brought together, a notch 270 can form a channel between the faces in which the non-target tissues can be protected from the juxtaposed faces. FIG. 31 illustrates an embodiment where notches 270 are formed into one face. When the arms are juxtaposed, the notices form a channel with the opposite face. FIG. 32 illustrates an embodiment where notches are formed into both faces and when the arms are juxtaposed the notches align to form channels 275.

The dimensions of a castration clamp can vary, usually depending upon the type or size of the patient to be treated. For example, a castration clamp for use on a bovine can be larger overall than a castration clamp intended to be utilized on a canine or feline. However, in certain embodiments, the configuration of the mortis and tenon and the channels in a castration clamp allows use on a range of patient sizes.

In one embodiment, a castration clamp is between approximately 3 inches and approximately 7.5 inches in length (L). In another embodiment, a castration clamp is between approximately 3 inches and approximately 4.5 inches in length. In another embodiment, a castration clamp is between approximately 5 inches and approximately 7.5 inches in length. In particular embodiment, a castration clamp is between approximately 4 inches and 6 inches in length.

Once a tissue clamp of the subject invention has been placed on the tissue and is exerting pressure against the tissue, the clamp 20 can be left in place on the tissue for a short amount of time to ensure that the tissue fuses or is sufficiently contused. This amount of time can vary, but is usually between approximately 2 minutes and approximately 3 minutes. For smaller tissue areas, it can take less than one minute for the tissue to fuse. Prior to removing the clamp, extraneous tissue, e.g., a polydactyl digit, or a tissue tag, can be excised from the surface of the clamp. Alternatively, tissue that is not intended to be removed, such as the scrotum, can be treated to prevent infection, disease, swelling, pain, or other issue that can arise after internal tissues are crushed. In both situations, these secondary procedures could also be done after the clamp is removed from the skin.

Figure 3:
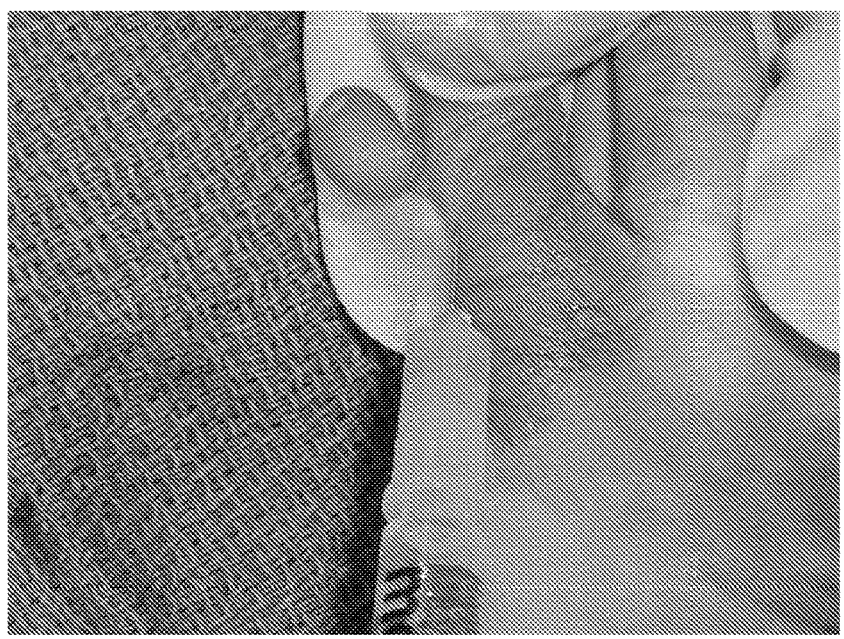
FIG. 3 is a photograph showing an anesthetic being injected into the area of a polydactyl digit of an infant. Note the pedical region to which a clamp of the subject invention can be applied.

With a hemostatic clamp, upon removal of the clamp, a skin tab 27 can be observed on the surface of the skin, such as shown, for example, in FIG. 5. In most situations, these entire procedures can be performed within 4-5 minutes, often in about 5 minutes. A local anesthetic can be applied topically and/or subcutaneously prior to initiation of a procedure, which is shown, for example, in FIG. 3. A 1% Lidocain solution can be effective for most polydactyl treatment procedures.

Figure 10A:
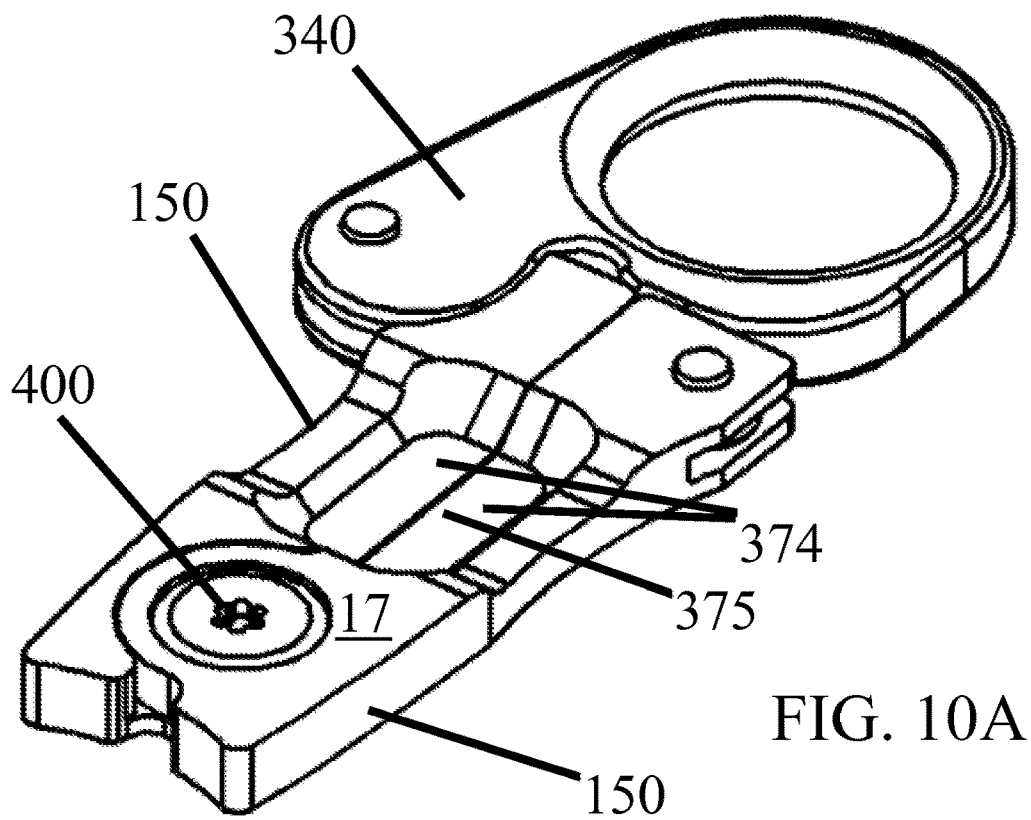
FIG. 10A is a perspective view of the front surface of an alternative embodiment of the subject invention.
Figure 10B:
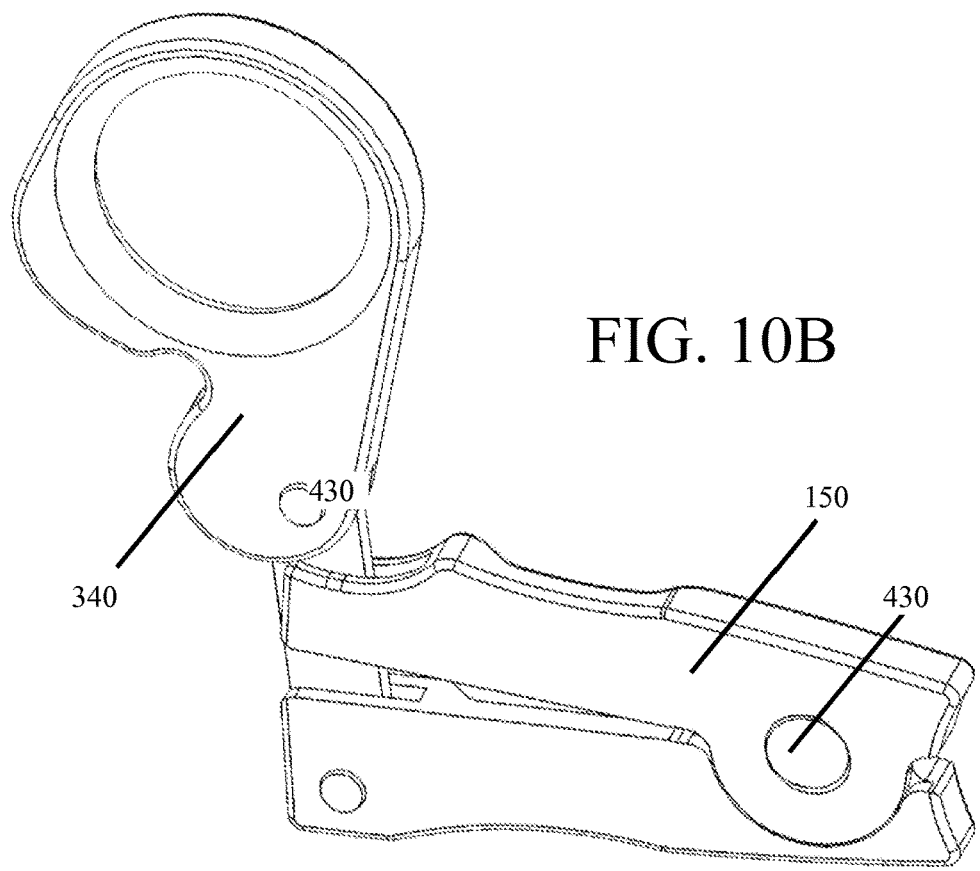
FIG. 10B is a perspective view of the rear surface of the alternative embodiment shown in FIG. 10A, with the toggle arm fully in place to juxtapose the arm faces.
Figure 11A:
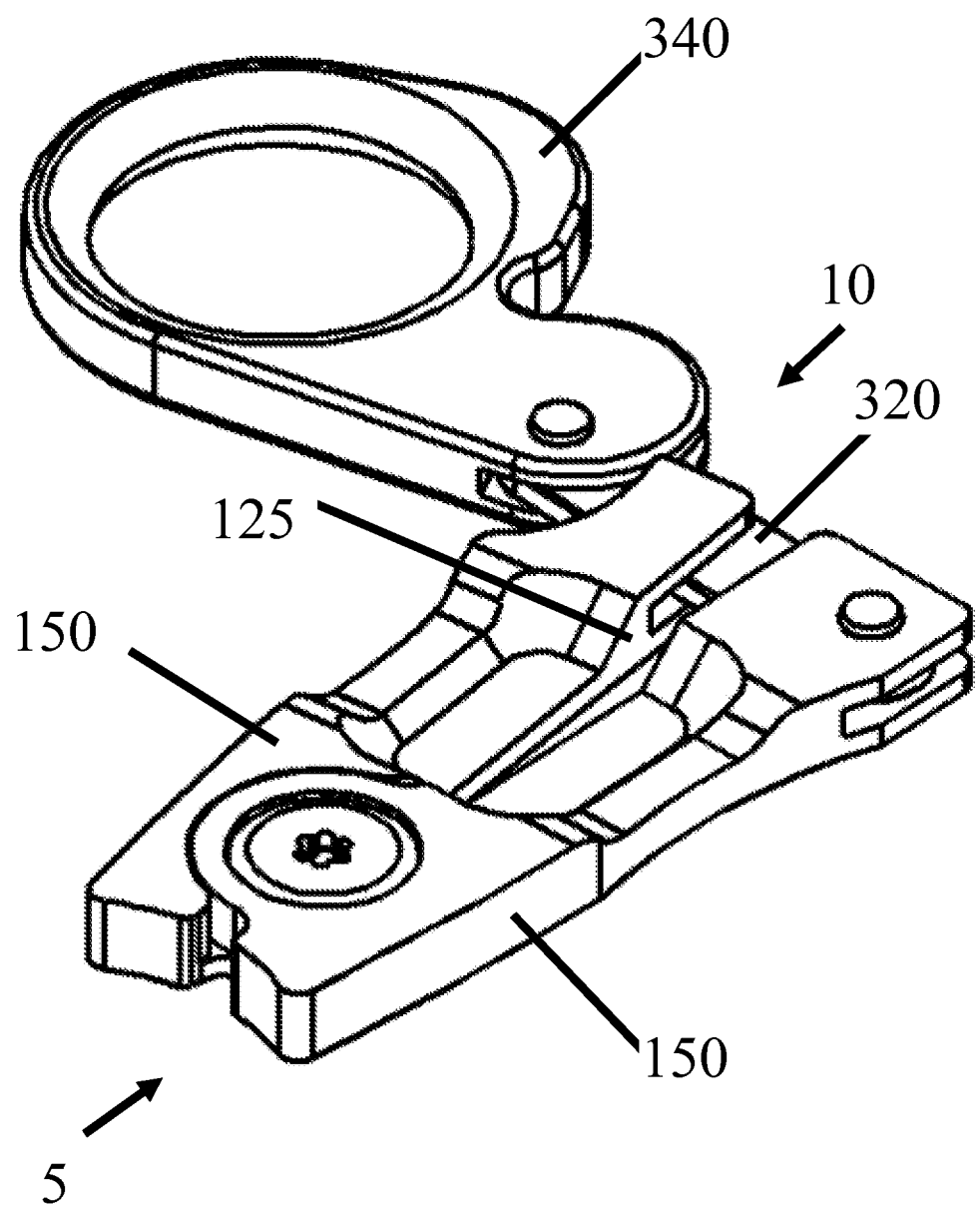
FIG. 11A is a perspective view of the embodiment in FIG. 10A, shown with the toggle arm in place in the longitudinal slots and toggle spindle unlatched.
Figure 11B:
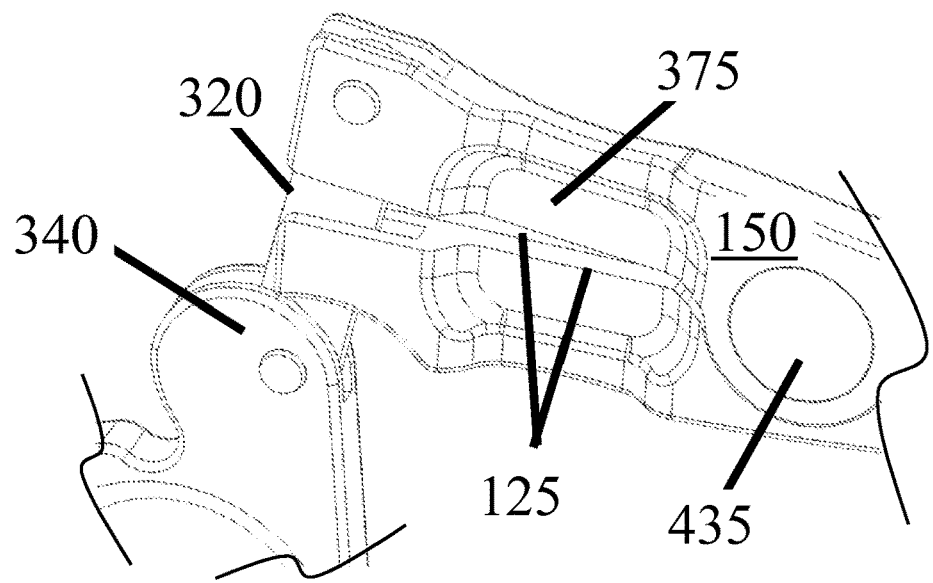
FIG. 11B is a perspective view of a portion of the front surface of the embodiment in FIG. 11A, demonstrating how the toggle arm fits into the longitudinal slots.
Figure 11C:
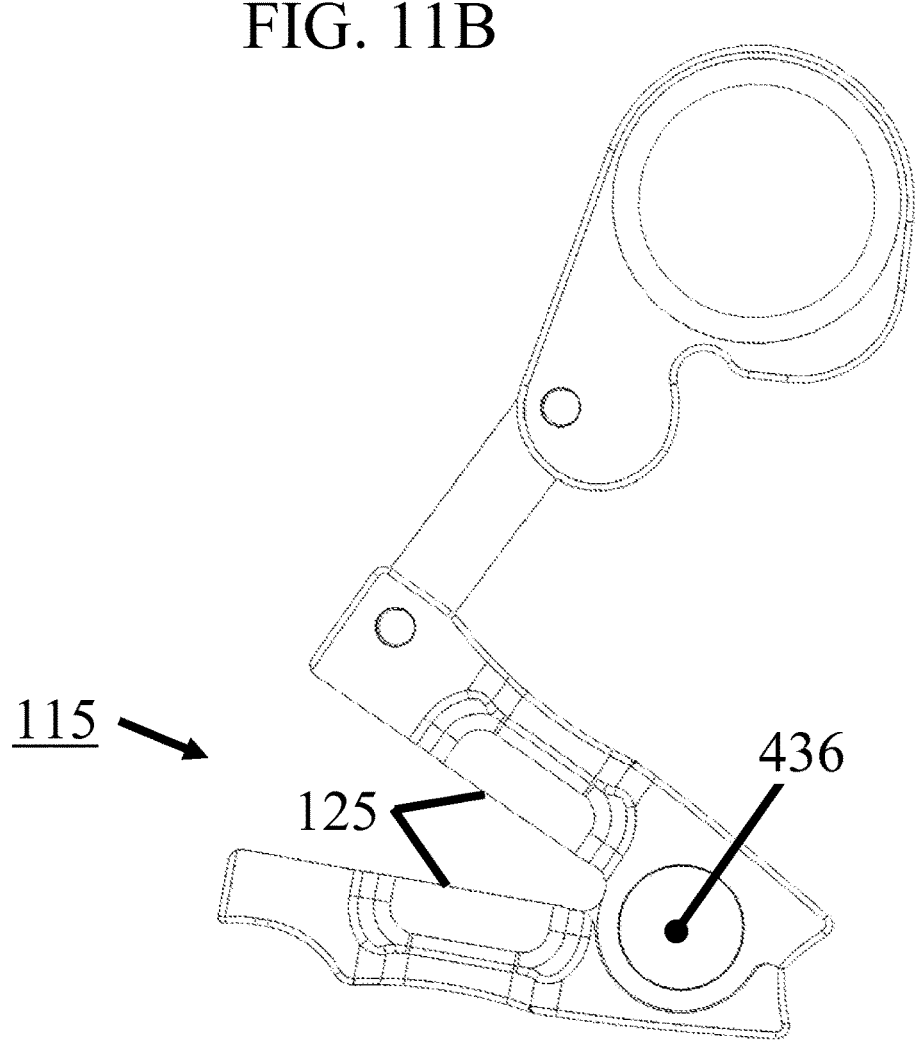
FIG. 11C is a side view of the embodiment shown in FIG. 11A.
Figure 13A:
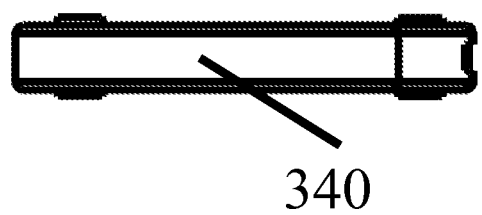
FIG. 13A is a bottom plan view of an embodiment of a hemostatic clamp according to the subject invention.
Figure 13B:
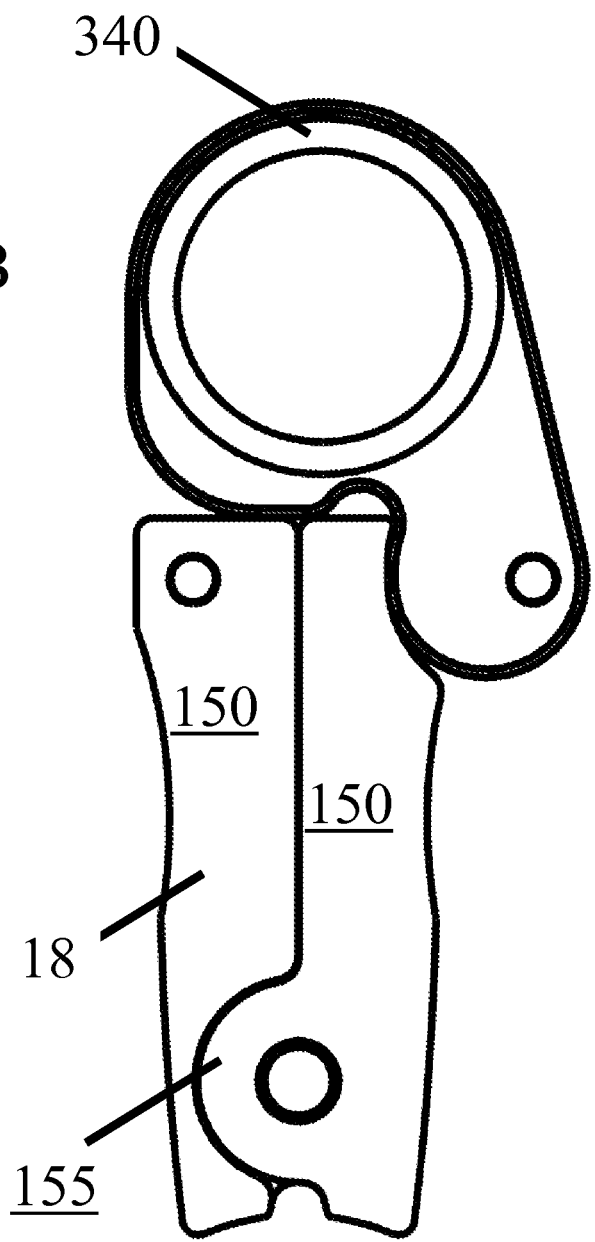
FIG. 13B is a front elevation view of the hemostatic clamp shown in FIG. 13A.
Figure 13C:
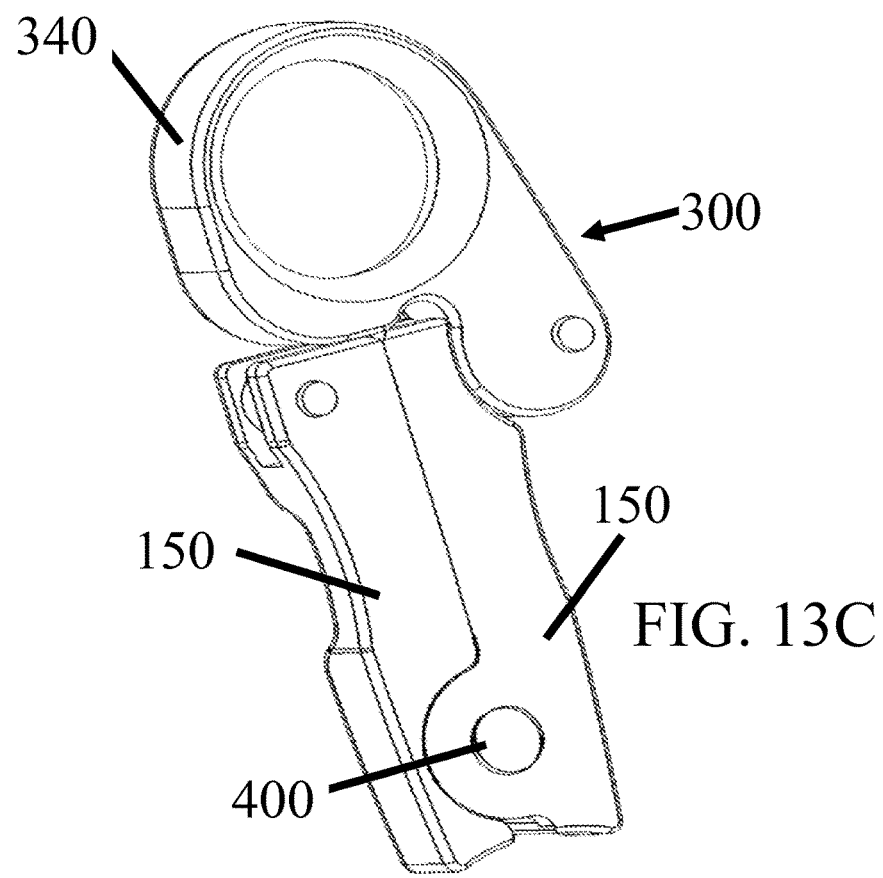
FIG. 13C is a front surface perspective view of a hemostatic clamp embodiment, according to the subject invention.
Figure 13D:
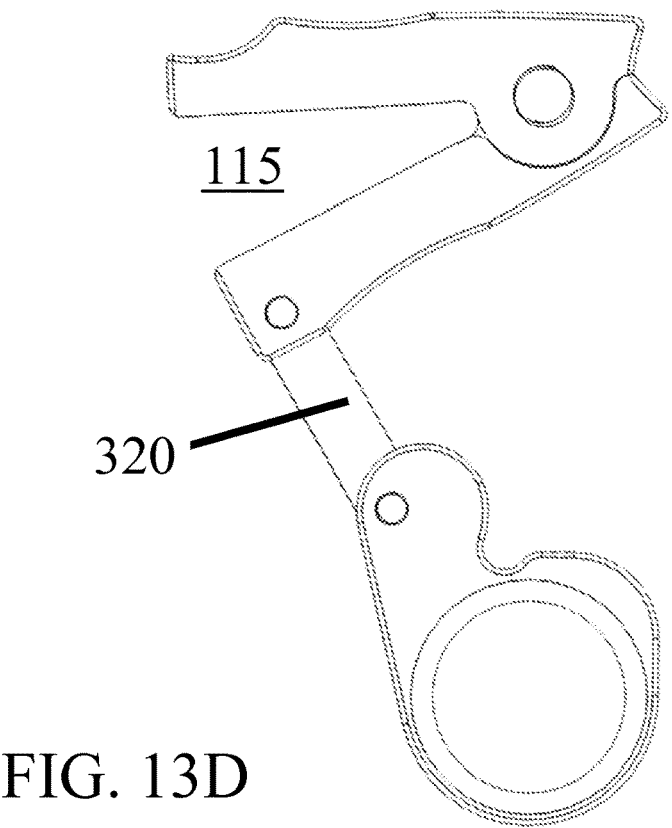
FIG. 13D is a top plan view of the embodiment shown in FIG. 13C with the toggle arm disengaged.
Figure 13E:
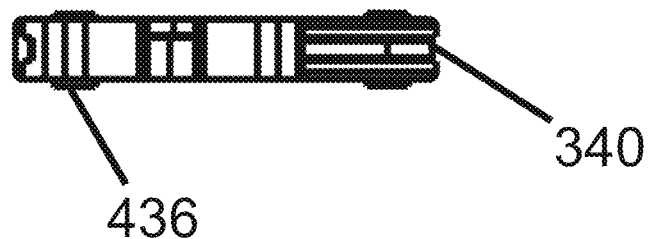
FIG. 13E is a bottom plan view of the embodiment shown in FIG. 13B
Figure 13F:
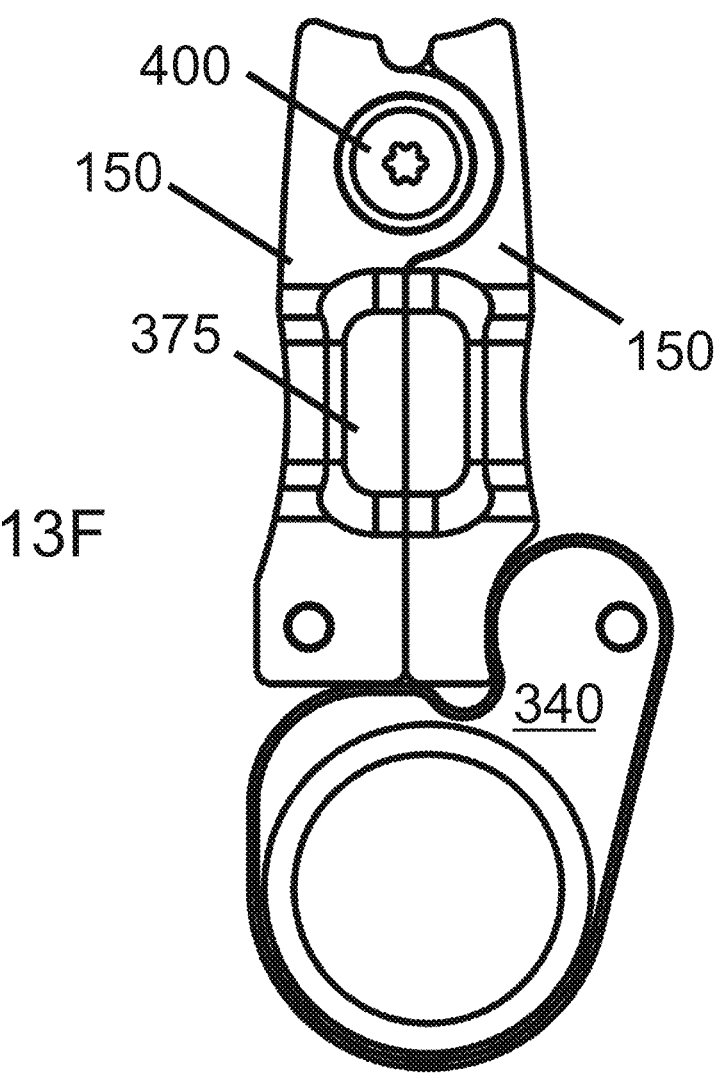
FIG. 13F is a front surface elevation view of the embodiment shown in FIG. 13E.
Figure 13G:
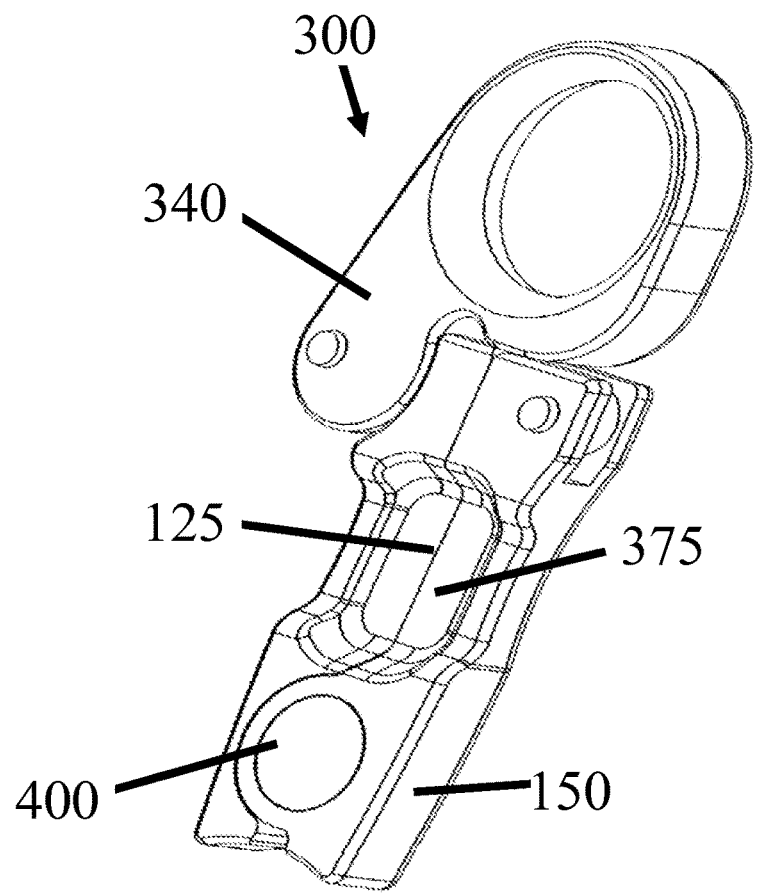
FIG. 13G is a side perspective view of the embodiment shown in FIG. 13F with the toggle arm and toggle spindle engaged with the arms.
Figure 13H:
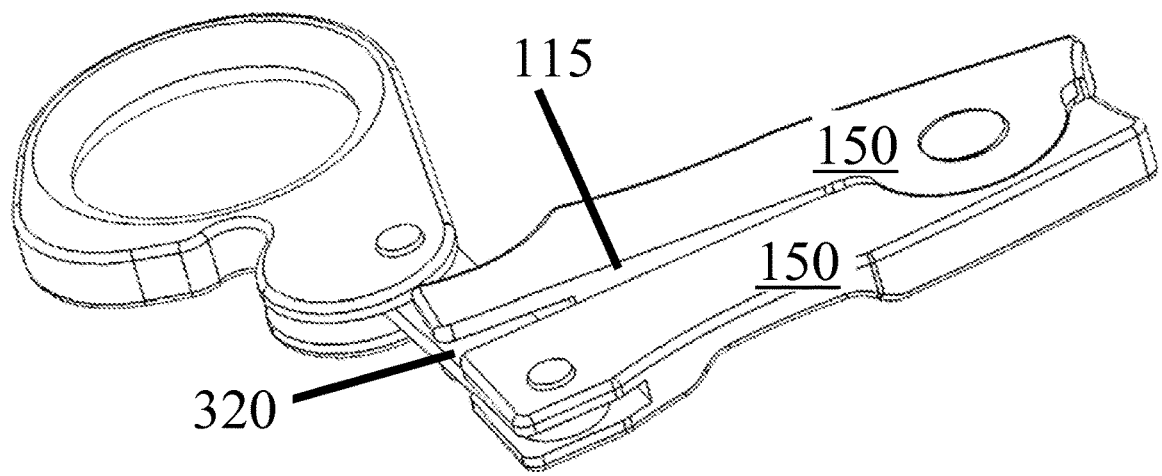
FIG. 13H is a side perspective view of the embodiment shown in FIG. 13G with the toggle arm engaged with the longitudinal slots and the toggle arm in position to be engaged.
Figures 13I, 13J:
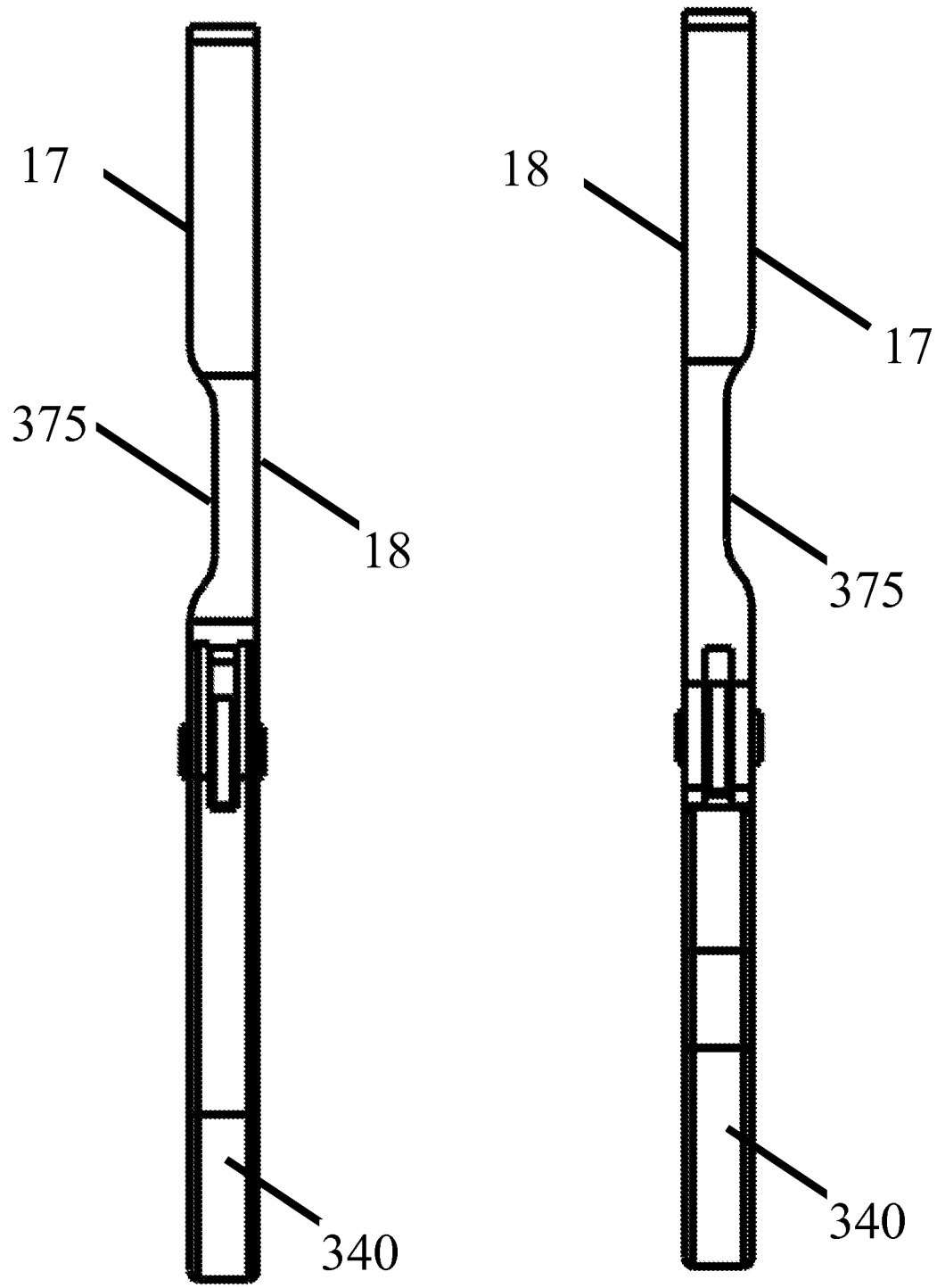
FIG. 13I is a side elevation view of the embodiment shown in FIG. 13F. This view is from the side where the toggle spindle presses against the arm.
FIG. 13J is a side elevation view of the embodiment shown in FIG. 13I. This view is from the side opposite to where the toggle spindle presses against the arm.
Figure 14:
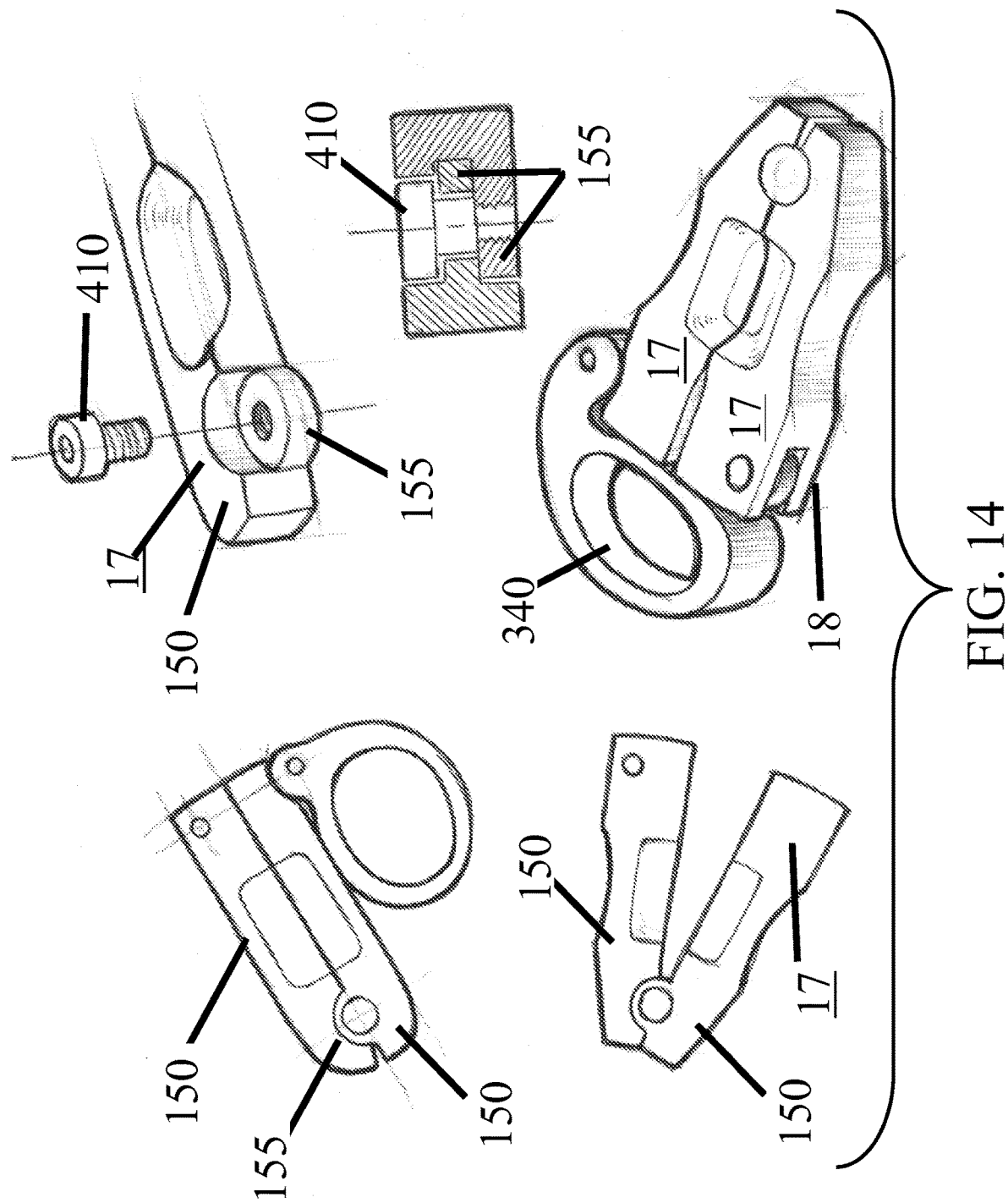
FIG. 14 illustrates embodiments of toggle spindle designs and rotation mechanism that can be used with the tissue clamp embodiments of the subject invention.

As mentioned above with regard to hemostatic clamp embodiments, the faces 125 of the arms contact the tissue so as to fuse it together. Thus, it is important that the amount of tissue area fused between the faces be sufficient to inhibit bleeding, but not leave an excessively large skin tab 27 upon removal. In one embodiment, the width of the face is approximately equivalent to the width of the arm, an example of which is shown in FIG. 2B. Alternatively, the width of at least some portion of a face can be less than the width of an arm, which is shown, for example, in FIGS. 1 and 13G. In one embodiment, there is a divit 375 within the front surface 17 and spanning between the arms 150, such that there is formed an area, between the arms, having a smaller thickness (T) than the arm. FIGS. 1, 10A, and 11A illustrate non-limiting examples of this embodiment, wherein each arm is formed with part of the divit, such that, when the arms are abutted, a full divit is formed on the front surface 17. Tissue can be aligned with the two halves of the divit, so that when the arms are closed over the tissue, the narrower face area forced by the divit creates a skin tab. The thickness (T) of the arm faces in the divit, which is the distance between the front surface and the rear surface, should be large enough to facilitate fusion of the skin and creation of a skin tab that is as small as possible. However, the thickness should not be so small that it becomes knife-like and causes actual severing or cutting of the skin. As mentioned above, the arms of a hemostatic clamp can have a thickness (T), between the front surface 17 and the rear surface 18, of between approximately $\frac{1}{10}$ inch and approximately $\frac{1}{4}$ inch. A divit can also have a width within these dimensions. A specific embodiment of the hemostatic clamp has a divit whose faces have a maximum thickness (T), between the front surface 17 and the rear surface 18, of approximately $\frac{3}{16}$ inch. More specifically, a divit has faces with a thickness of approximately $\frac{2}{16}$ inch.

As mentioned above, embodiments of the subject invention can be made disposable. Alternatively, they can be made partially disposable, where some portion of the clamp can be removed and disposed, while another part is retained and reused. There are known any of a variety of disposable materials that can be used for a clamp or part of a clamp of the subject invention. Such materials, used alone or together, can provide the necessary rigidity and strength to withstand the amount of force necessary to properly fuse a tissue. Those same materials can be sufficiently economical that a tissue clamp of the subject invention can fully, or at least partially, disposable. Examples of such materials can be, but are not limited to, nylon, ceramics, metals, high density plastics, tempered glass, and other materials, or combinations thereof, known to those with skill in the art.

Further, such disposable or partially disposable embodiments can be part of a kit that can include an appropriate sharp implement for removing the excess tissue or digit. A kit could further include one or more pharmaceuticals, medical devices, or treatment materials, or other medically-related supplied useable for treating the tissue before, during, or after receiving treatment with a clamp of the subject invention. By way of non-limiting example, pain killers, antiseptics, topical antibiotics, (e.g., silver nitrate solutions) coagulants (in the event of minor bleeding), bandages, swabs, gauze, tape, and other items or materials known to those with skill in the art, could be included in such a kit. It is within the skill of a person trained in the art to determine what materials could compose a kit that includes a tissue clamp of the subject invention. Such variations are within the scope of this invention.

Figure 26A:
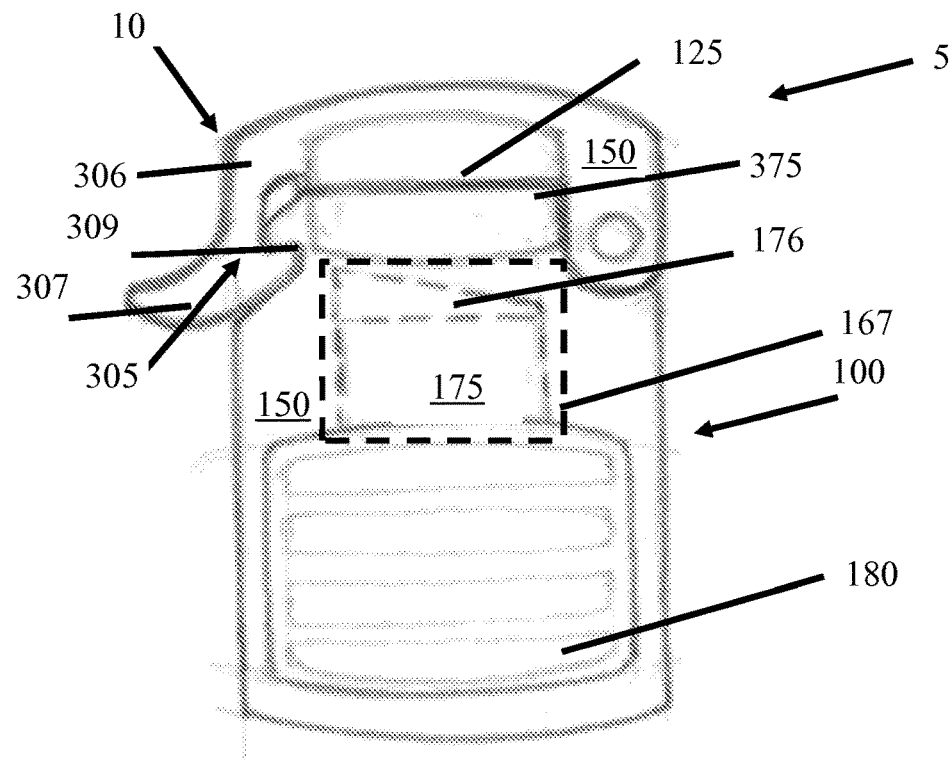
FIGS. 26A and 26B illustrate an embodiment of a hemostatic tissue clamp having a recessed blade incorporated therein, according to the subject invention. In this embodiment, the blade is moved perpendicular to the arm faces.
Figure 26B:
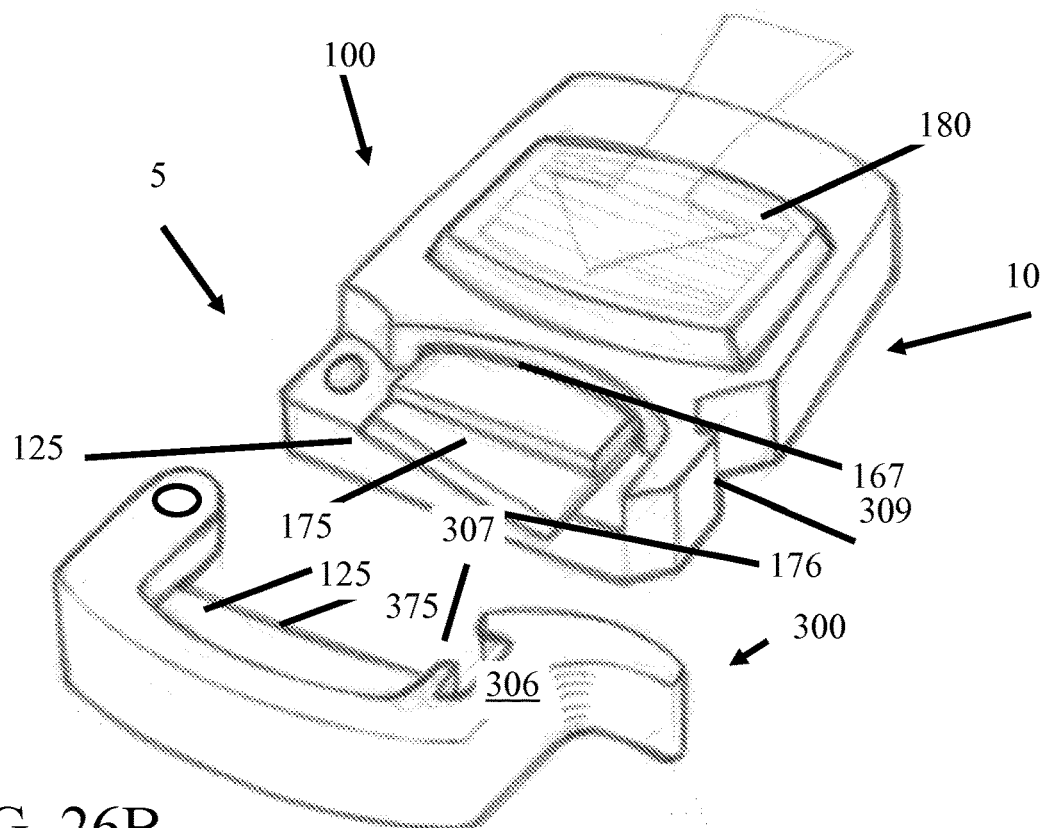
Figure 28A:
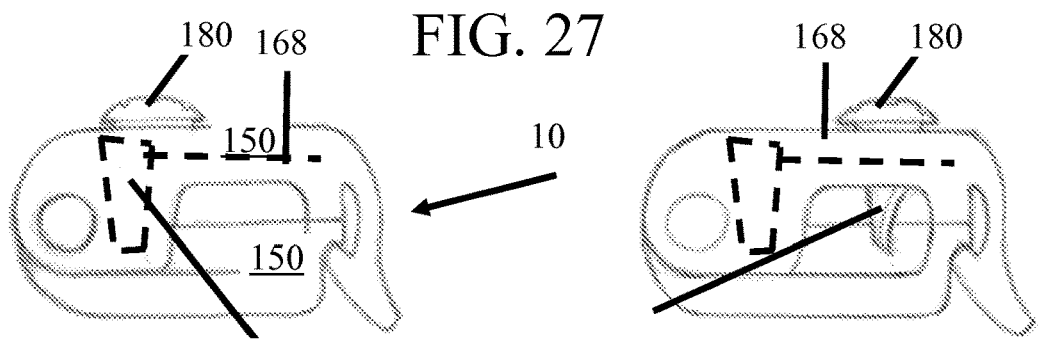
FIGS. 28A, 28B, and 28C illustrate another alternative embodiment of a hemostatic tissue clamp having a recessed blade. In these figures it can be seen how the blade is recessed into the arm and can be moved out and over the divit surface. In this embodiment, the blade is moved substantially parallel or in the same direction as arm faces.
Figure 28B:
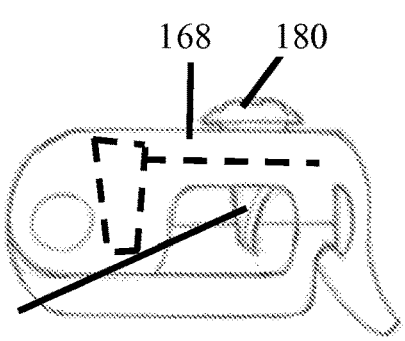
Figure 28C:
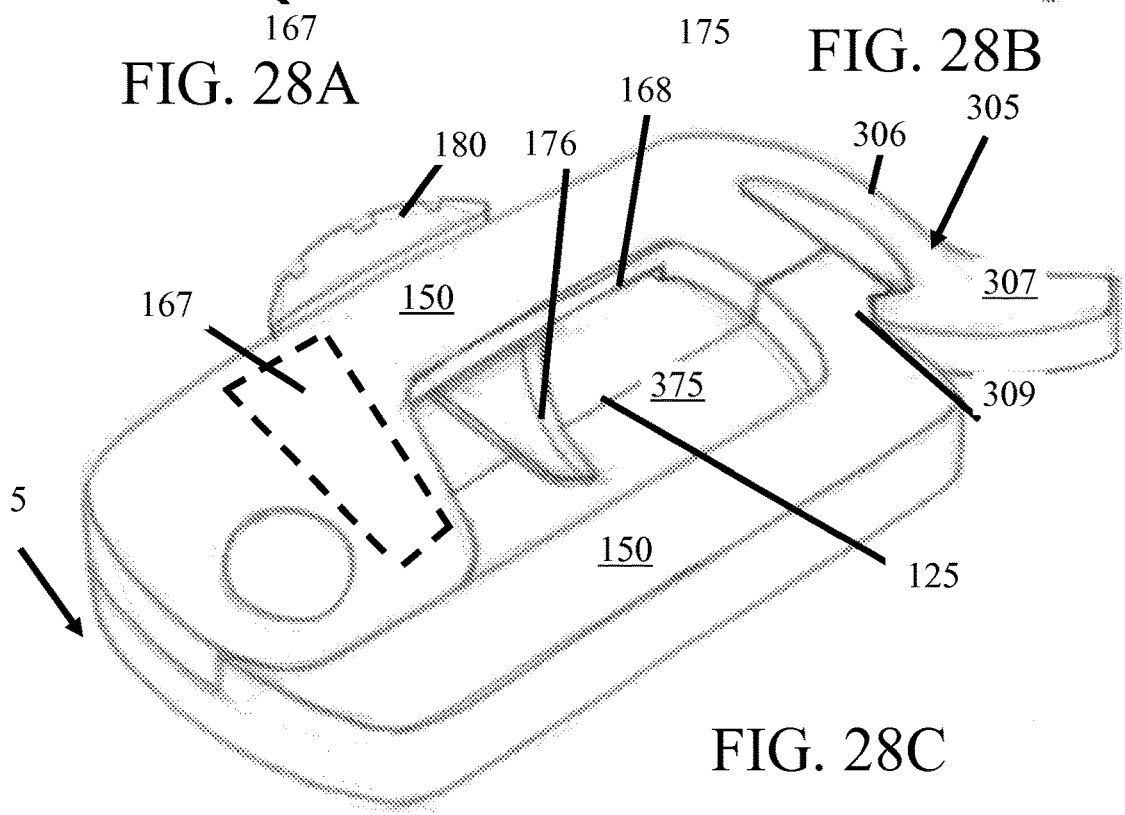
Figure 29A:
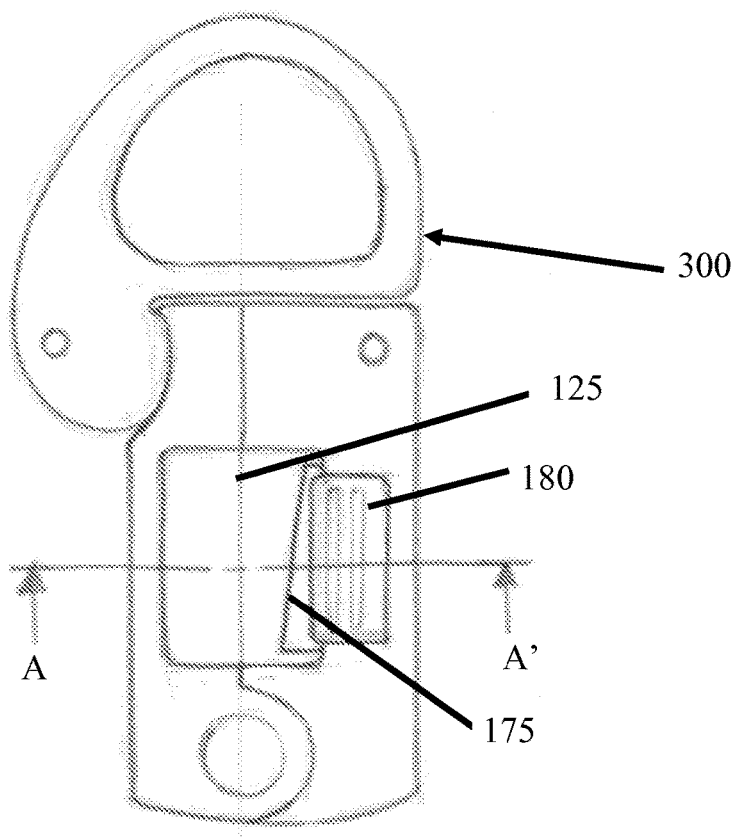
FIGS. 29A, 29B, and 29C illustrates another alternative embodiment of a hemostatic tissue clamp having a non-recessed blade. In this embodiment, the blade moves perpendicular to the arm faces.
Figure 29C:
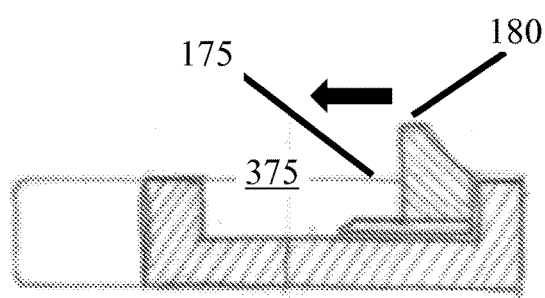
Figure 29B:
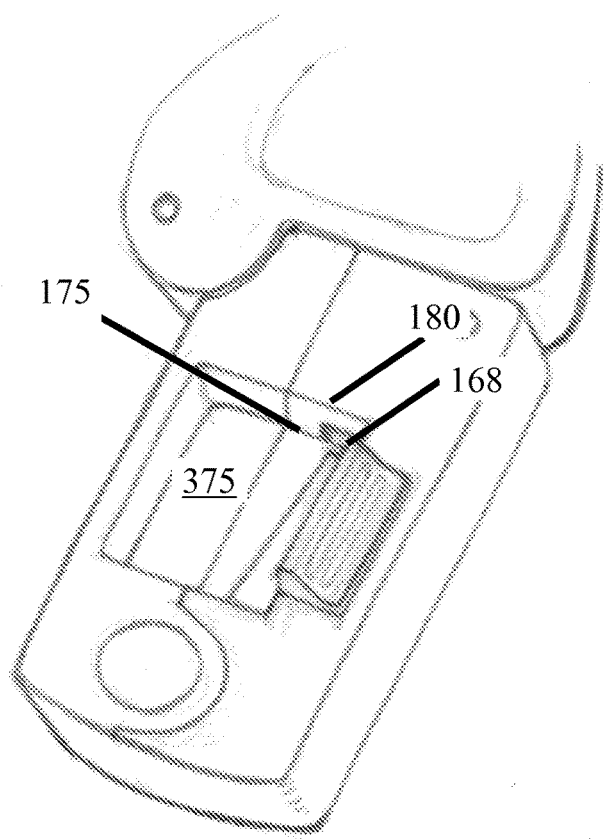

While a scalpel or other cutting implement can be used to excise tissue. It can be advantageous if the scalpel or other blade was incorporated or made integral with a tissue clamp. This could provide a single unit device that was convenient to use and if made disposable, the blade and tissue clamp could be discarded simultaneously. In one embodiment, a hemostatic clamp 100 has incorporated therein a sliding blade 175. A sliding blade can be planar with the front surface 17 of a divit 375, such that when a tissue is extending from between the arm faces 125 after a clamp has been locked, the sliding blade can be used to move across the front surface of the divit and cut the extraneous tissue. In one embodiment, shown for example, in FIGS. 26A and 26B, the sliding blade can move perpendicular to the faces. For the purposes of illustration, FIG. 26B shows the arms separated, so that the position of a blade 175 when extended perpendicular to the arm faces can be more easily seen. FIGS. 29A, 29B, and 29C illustrate another embodiment of a blade that can be moved perpendicular to the arm faces 125. In an alternative embodiment, a blade can move parallel or substantially parallel or colliner to the arm faces, as shown, for example, in FIGS. 27, 28A, 28B and 28C.

In a particular embodiment, the blade is operably engaged with a track 168 in which the blade moves in a linear direction parallel with, or at least substantially parallel with, the arm. The track can be, in general, a channel within an arm. A blade can extend through the track so that it protrudes through the channel and across the divit. FIGS. 28C and 29B show examples of tracks in which a blade has been operably engaged and can follow the track to perform a cutting operation.

The cutting edge 176 of a blade 175 can also be configured so as to provide a slicing motion as it moves through tissue. FIGS. 26A and 26B, as well as FIGS. 29A-29C, illustrate examples of a blade having an angled cutting edge 176. FIGS. 27, 28A, 28B, and 28C illustrate an example of a blade having a curved cutting edge 176. The cutting edge of a blade can have other configurations, including, but not limited to, serrations. In addition, the size or length of the cutting edge can depend upon the size of the divit, the direction of movement of the blade edge, the size of the tissue the clamp is used with, and other factors understood by those with skill in the art. In one embodiment, the cutting edge 176 of a blade 175 extends across more than 50% of the divit length (L). In a more specific embodiment, the cutting edge 176 of a blade 175 extends across more than 75% of the divit length (L). In a still more specific embodiment, the cutting edge of a blade extends across at least 90% of the length (L) of a divit. It will be understood that variations in the length of a cutting edge, other than those described, are within the scope of this invention.

Figure 27:
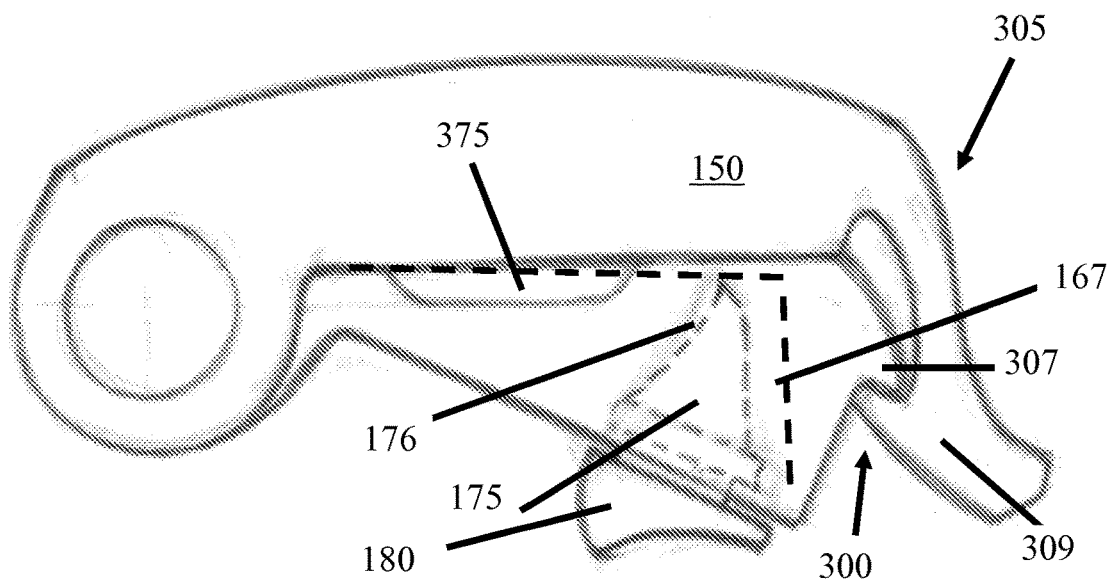
FIG. 27 illustrates an alternative embodiment of a hemostatic tissue clamp having a recessed blade incorporated therein, according to the subject invention.

In a further embodiment, the blade 175 incorporated with a hemostatic clamp 100 is recessed or hidden within an arm 150 of the blade. This can prevent accidental contact with the cutting edge 176 and provide for safer disposal and storage. In a particular embodiment, an arm 150 has an internal chamber 167 in which the blade can be recessed or temporarily stored until it is removed or slide across the divit surface. In a further embodiment, the internal chamber is contiguous with the track 168, such that the blade can move along the track into the internal chamber. FIG. 26A illustrates one example of an internal chamber 167 within an arm 150 of a hemostatic clamp. FIG. 27 illustrates another embodiment of an internal chamber 167. FIGS. 28A-28C illustrate yet another embodiment of an internal chamber.

The movement of a blade across the facing surface of a divit can be accomplished with the use of an attachment by which the blade can be manually moved. In one embodiment, a slider 180 is fixedly attached to a blade 175. A slider can be used to move the blade in the direction for cutting tissue. A slider can be a rigid or semi-rigid extension, such as, for example, a button attached to one edge of a blade. In a particular embodiment, the slider can be affixed to the blade so that it extends from the opposite end of the track 168, described above, that the blade protrudes from. Pushing the slider on one side of the track can move the blade in the same direction on the other side of the track. FIGS. 26A, 26B, 27, and 28A-28C all illustrate examples of sliders that can be used with a blade, recessed or otherwise, to move the blade in a cutting direction. FIGS. 28A and 28B illustrate how the slider can be used to move the blade through a track.

The use of recessed blades and sliders are well-known in the art. There are a myriad of devices that employ the use of a recessed blade and a slider, such as a button, to move the blade. It is within the skill of a person trained in the art, having benefit of the subject disclosure, to determine how a blade can be recessed into the arm of a hemostatic clamp and the attachment of a slider to control the motion of the blade. Such variations, which provide the same function, in substantially the same way, with substantially the same result, are within the scope of this invention. The hemostatic clamp of the subject invention is particularly amenable for removal of polydactyl digits; however, it can also be utilized for the removal of other types of tissues from the surface of the body. It can be preferable for such tissues to be covered with skin, so as to promote fusion of the skin, as described above. The general diameter of a tissue that can be removed with a hemostatic clamp 20 is approximately 20 cm. or less.

Once positioned and in contact with a tissue, a clamp of the subject invention will ideally be left in place for at least a few minutes, as mentioned above. To properly fuse or crush the tissue, the amount of pressure applied should be sufficient and consistent. To ensure this, the arms can be locked into place over the tissue area. Ideally, the locking mechanism 300 will be easy to manipulate and will maintain a consistent, even pressure on the arms and force the faces 125 together. A locking mechanism utilized with the embodiments of the subject invention should not interfere with the operation of the arms or undesirably inhibit the insertion of a tissue into the mouth 115. Further, a locking mechanism should be easy to manipulate so that once the clamp is positioned on a tissue, engaging the locking mechanism will not alter the position of the clamp. One advantage of the embodiments of the subject invention is the compact size of the device. Therefore, a locking mechanism will, ideally, be functional without having to increase the size of the clamp. The amount of pressure required to fuse or crimp tissue can vary depending upon the type of tissue, location, and other factors known to those with skill in the art. In one embodiment, the amount of pressure applied by the abutted faces of a tissue clamp of the subject invention is at least about 25 p.s.i. and can be at least 50 p.s.i., 75 p.s.i., 100 p.s.i, or 150 p.s.i. and/or a p.s.i. in a range between any two of the listed values.

In one embodiment, a snap clamp 305 can be used to secure the arms after being closed over a tissue. A snap clamp can have a snap clamp arm 306 fixedly attached to one arm 150 at or near to the distal end 10 of the mouth 115 of the tissue clamp. The other end of the snap clamp arm 306 can include a pawl 307 that engages with a tooth 309 located on the opposite arm of the tissue clamp. When the snap clamp arm is rotated over the closed mouth of the clamp, the pawl can engage with the tooth, as shown, for example, in FIGS. 26A and 28C, to hold the abutted faces together with sufficient force to fuse a tissue therebetween. Snap clamp devices are known in the art. Variations which provide the same functionality are within the scope of this invention.

In another embodiment, a toggle lock is employed as a locking mechanism 300 to secure the arms during a procedure. Toggle locks are known in the art and employ an "over the center" principle of operation, wherein a geometrical linkage is used to amplify a low input user force into a high input clamping force. Toggle locks are well known as a mechanism for connecting and applying pressure between two objects. Toggle locks usually employ a toggle arm operably connected at a first end to the one object and the second end operably attached to a toggle spindle. The toggle spindle has a specific shape and size, usually oval, to which the second end of the toggle arm is connected. In operation, the toggle arm extends across both objects and force is applied to the toggle spindle in a direction that forces it to rotate, often, but not necessarily, against the second object, causing the toggle arm to be pulled toward and over the toggle spindle, which forces the first object to press against the second object in the direction of the toggle arm. When sufficient force is applied to the spindle toggle, it will rotate past the geometric center of the larger diameter of the spindle, creating a positive lock and preventing the spindle from rotating backwards when force is no longer applied. FIGS. 2A and 2B illustrate examples of toggle lock embodiments that can be used with the subject invention. With these embodiments, a first end 322 of a toggle arm 320 is operably connected to a first arm of the clamp. If the toggle arm is a rigid piece, the operable connection mechanism 325 can allow the toggle arm to rotate. If the toggle arm is a flexible piece, the operable connection mechanism 325 to the first arm can be fixed, such that the toggle arm flexes or wraps from the first arm to the second arm.

The toggle lock can further comprise a toggle spindle 340 that is operably connected to a second end 324 of the toggle arm 320. If the toggle arm is rigid, the toggle spindle can be rotatably attached. If the toggle arm is flexible, the toggle spindle can be fixedly attached and the toggle arm will wrap over the spindle. It can be seen in FIGS. 2A and 2B that a toggle spindle of the subject invention is non-circular, such that there is a major axis 341 and a minor axis 343 to the spindle. In a specific embodiment, the toggle spindle has a minor axis that is approximately ½ inch and a major axis that is approximately ¾ inch.

With this embodiment, the toggle arm is positioned across the distal ends 10 of the arms 150 of the clamp, as indicated in FIG. 2A and FIG. 4. The toggle spindle is then forcibly rotated, usually by means of the lever 345, until the second end of the toggle arm is forced over or past the larger axis of the toggle spindle. As the toggle spindle rotates it forces the arms 150 to be pressed together in the direction of the toggle arm, which causes the faces 125 to be forcibly juxtaposed. Any tissue within the mouth 115 will subsequently be compressed between the faces. In a specific embodiment, the major axis of the toggle spindle is rotated between approximately 45° and approximately 90° to engage the positive lock position.

Figure 18:
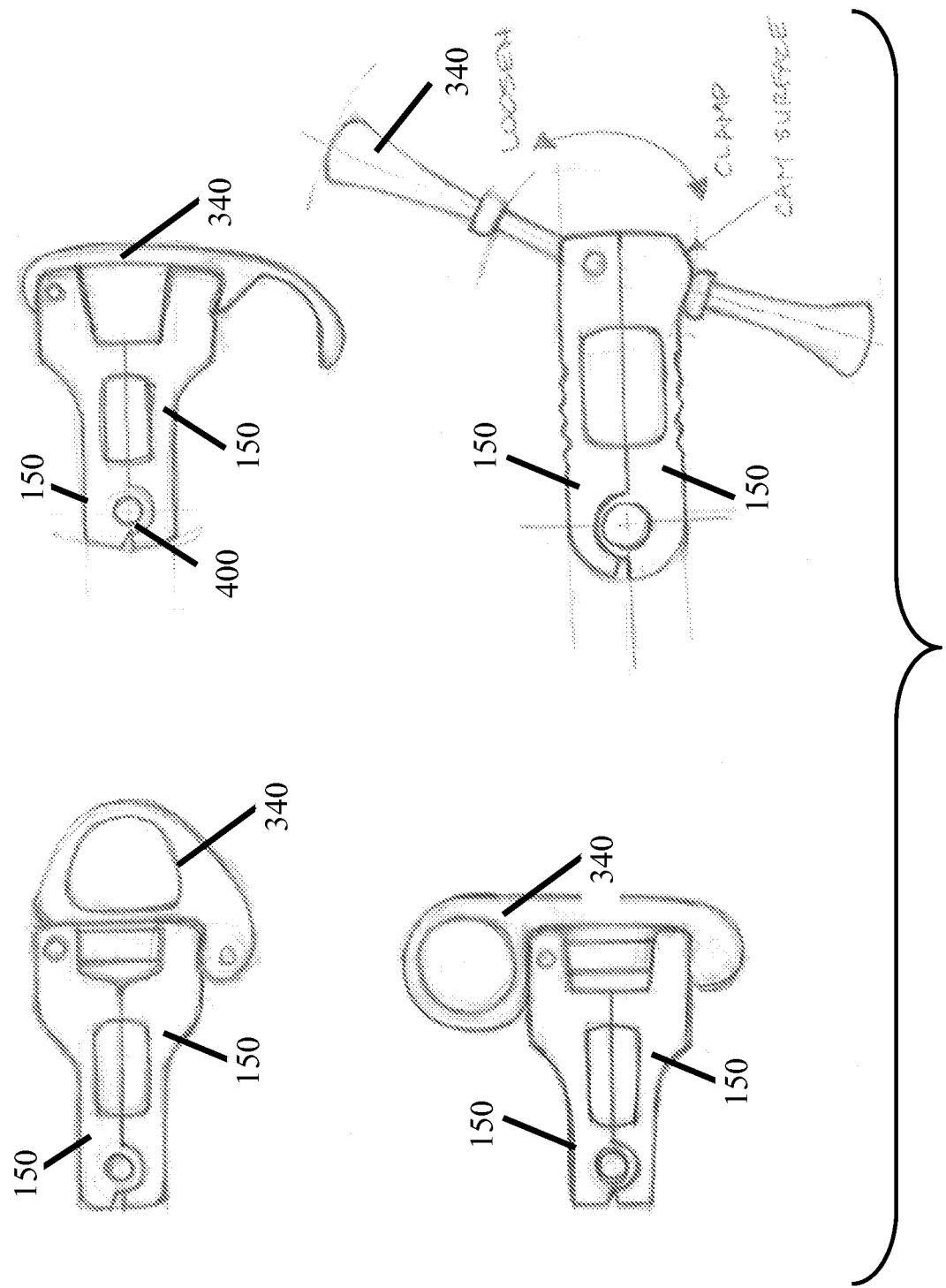
FIG. 18 illustrates alternative toggle spindle embodiments that can be used with the tissue clamp embodiments of the subject invention.
Figure 19:
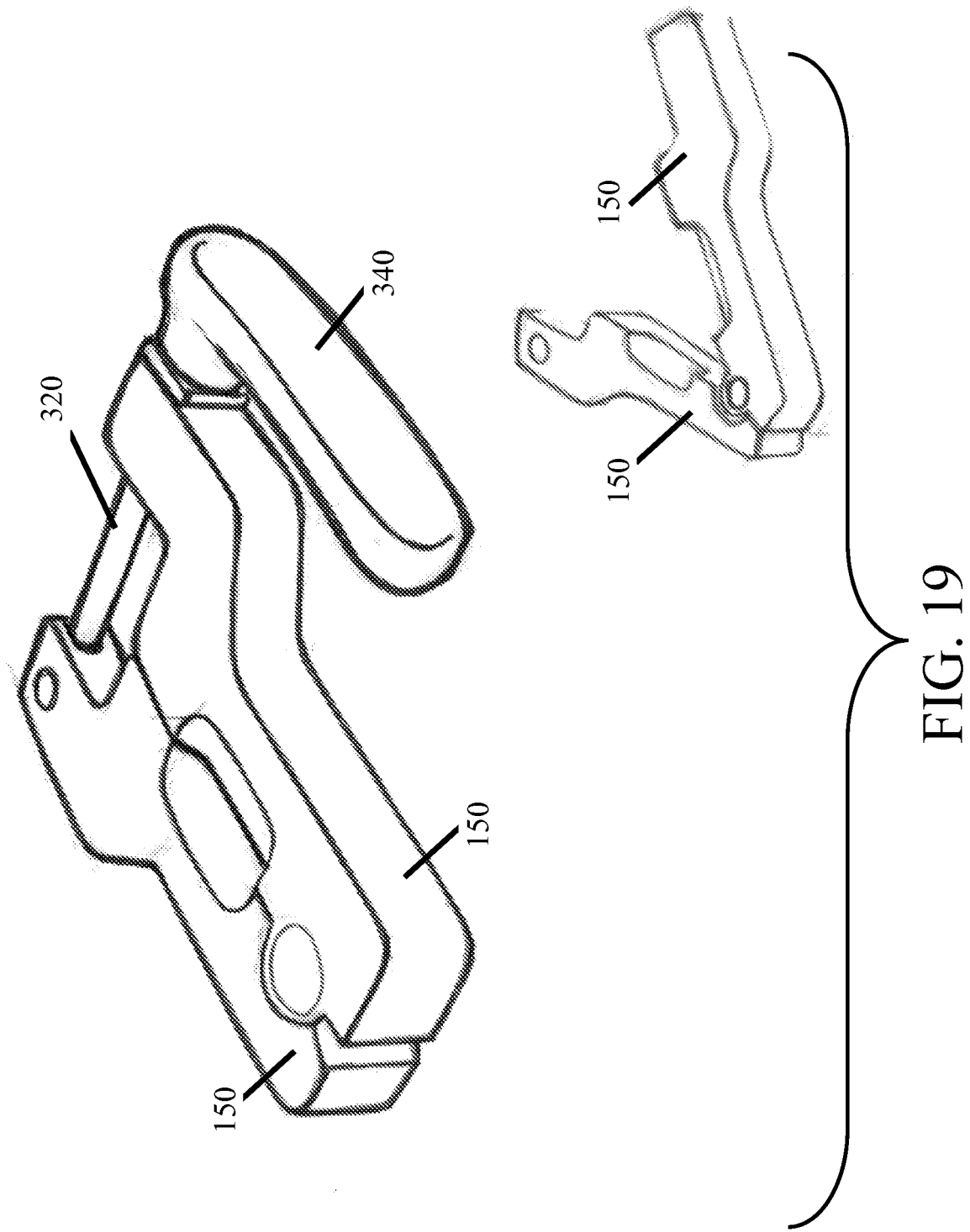
FIG. 19 illustrates an embodiment with a handle-shaped toggle arm design.
Figure 20:
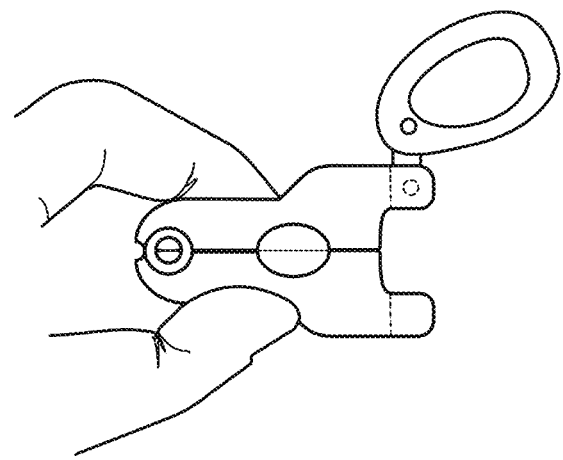
FIG. 20 illustrates the use of an embodiment of a tissue clamp having a toggle lock, according to the subject invention.
Figure 21:
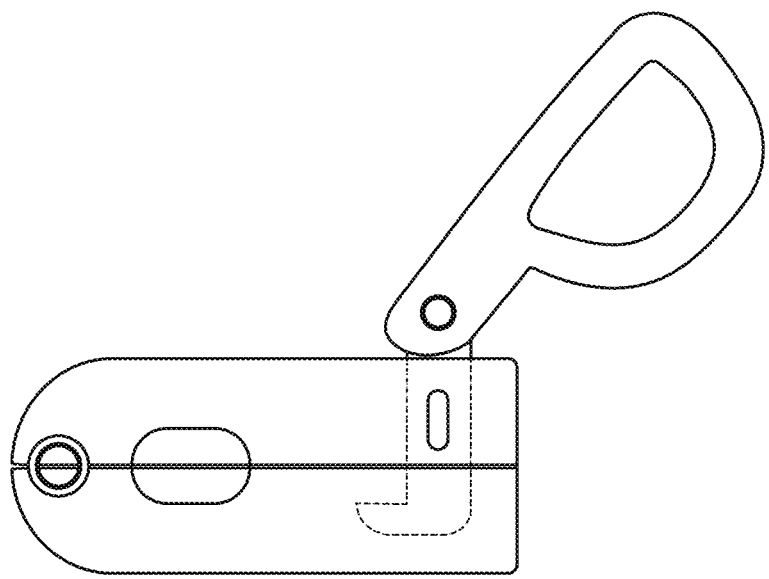
FIG. 21 illustrates an alternative design embodiment of a tissue clamp, according to the subject invention.
Figure 22:
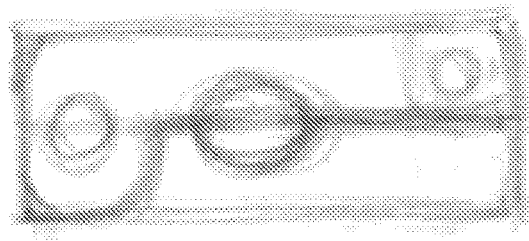
FIG. 22 illustrates an alternative design embodiment of a tissue clamp, according to the subject invention.
Figure 23:
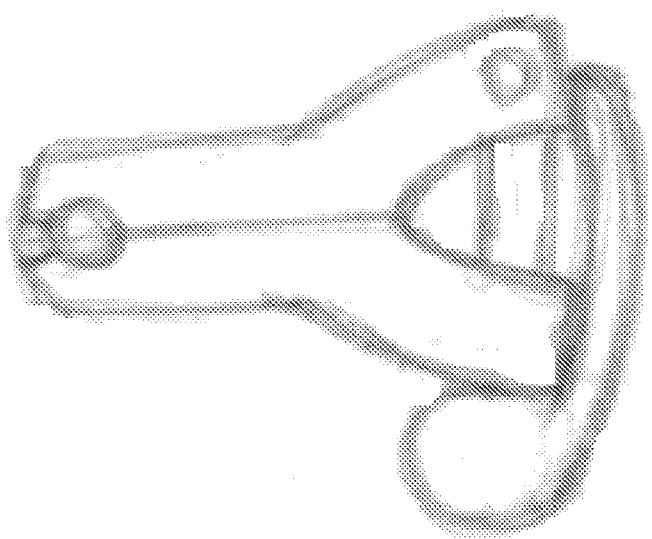
FIG. 23 illustrates an alternative design embodiment of a tissue clamp utilizing a toggle lock, according to the subject invention.
Figure 24:
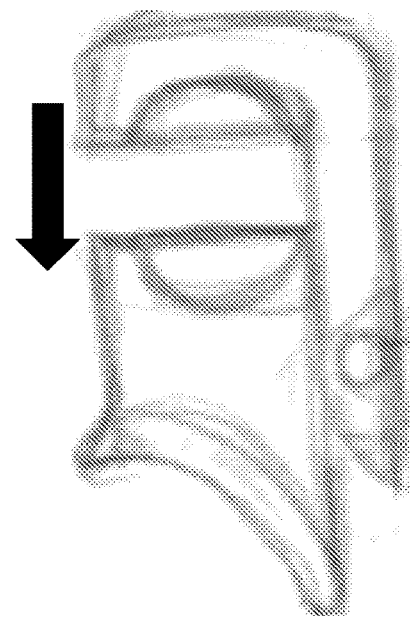
FIG. 24 illustrates an alternative design embodiment of a tissue clamp where one arm is slidably engaged with the opposite arm of a tissue clamp.
Figure 25:
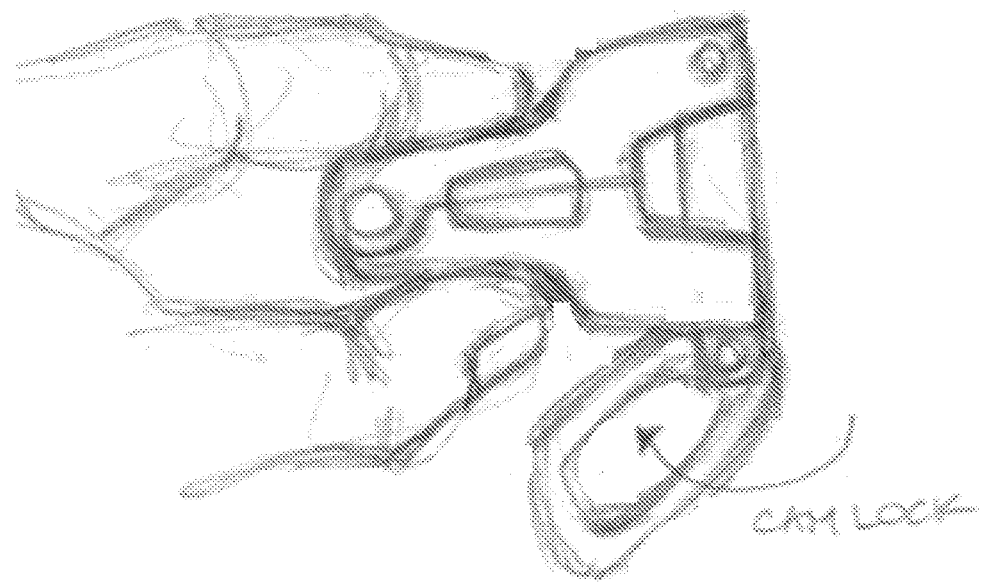
FIG. 25 illustrates an alternative design embodiment of a tissue clamp utilizing a toggle lock, where the toggle spindle locks against the side edge of an arm, according to the subject invention.

In a further embodiment, the distal ends 10 of the arms 150 are adapted to receive the toggle arm. In one embodiment, the distal ends of the arms are configured with longitudinal slots 350 into which the toggle arm 320 can be aligned. The slot can prevent the toggle arm from slipping or dislodging from the proximal ends of the arms when force is applied to the toggle spindle. In a specific embodiment, the slot is approximately ⅛ inch wide. There are numerous types of locking mechanisms and/or guides that can be utilized with the devices of the subject invention. FIGS. 18 and 19 illustrate several other types of locking mechanisms that utilize different toggle arm designs. Each of these different designs can operate on the same principle described above. As mentioned above, such locking mechanisms should not inhibit operation of the clamp and will provide sufficient force to juxtapose the faces sufficiently to fuse any tissue therebetween. A person with skill in the art would be able to determine one or more locking mechanisms and/or guides that can be used with the embodiments of the subject invention.

In some instances, it can be beneficial to be able to control the amount of pressure applied to a tissue. Depending upon the amount or size of the tissue to be removed, more or less pressure may be needed to ensure proper tissue fusion and not crush or contuse the tissue. A locking mechanism 300 that can abut the arms and provide more control over pressure can be used instead of a clamp.

One embodiment employs a nut and bolt configuration 500. In a particular embodiment, the nut and bolt configuration is located at the second end 324 of the toggle arm 320, an example of which is shown in FIG. 9. With this embodiment, the toggle arm can be engaged with the longitudinal slots 350, as described above. The second end of the toggle arm 320 can extend past the longitudinal slot in which it is engaged. That extending portion of the toggle arm can have threads 420, or an equivalent thereof, for engagement with a nut 425 or other tightening device. Ideally, the nut can be ergonomically designed to be easily manipulated and secured to the threaded portion of the toggle arm. A wing nut is one example of an ergonomic design that can be utilized with this embodiment.

With the arms abutted and the toggle arm in place in the longitudinal slots, the nut can be engaged with the threads and advanced onto the toggle arm until it makes contact with the arm. At this point, the nut can be tightened against the arm to increase pressure between the faces 125. The nut can continue to be advanced until sufficient pressure is applied to the tissue. The contact between the nut and the arm can prevent the nut from coming unscrewed, thus, locking it at the desired location. In a further embodiment, a deformable material 530 can be employed between the nut and the arm to increase friction between the components and ensure that the nut does not disengage from the toggle arm. A variety of deformable materials can be employed for this purpose, such as, for example, elastomeric materials, metals, ceramics, plastics, and other materials known to those with skill in the art.

Figure 30A:
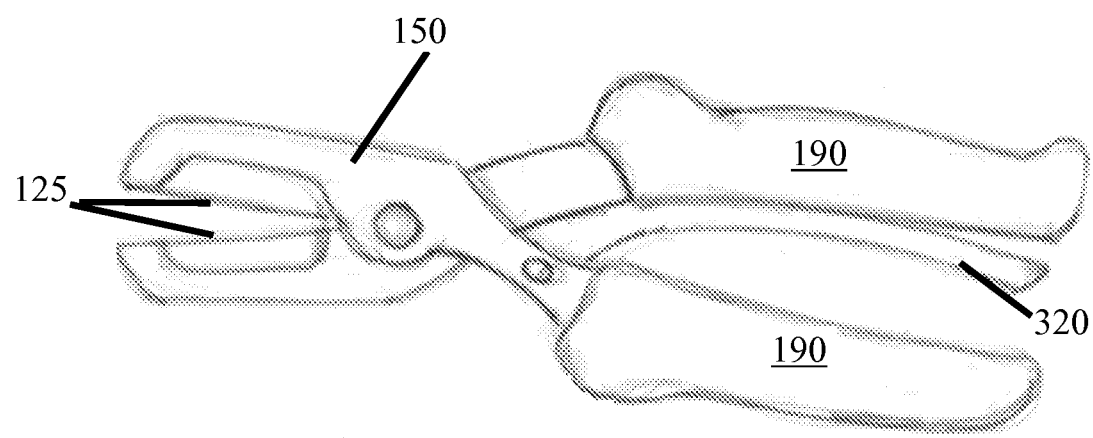
FIGS. 30A and 30B illustrate an embodiment of a hemostatic clamp that utilizes handles to open and close the arms of the clamp.
Figure 30B:
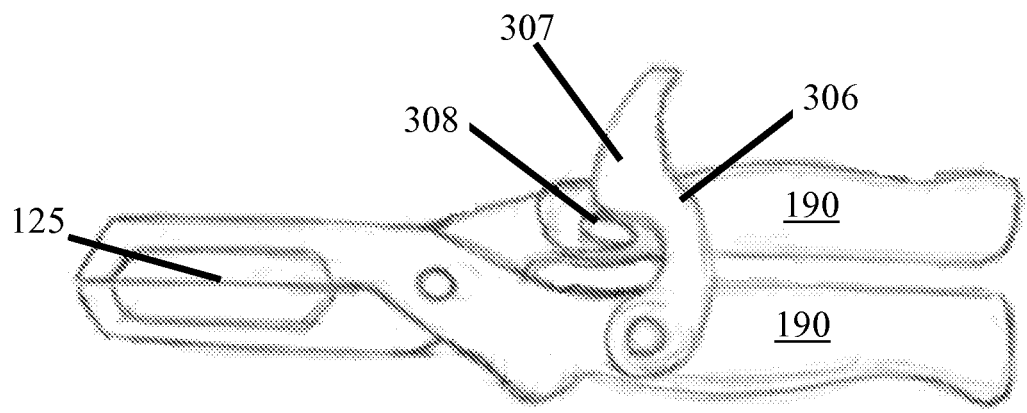

FIGS. 30A and 30B illustrate an alternative embodiment of a tissue clamp where the arms 150 are configured to have handles 190 at the proximal end 10. The handles can be squeezed together to close the arm faces 175. FIG. 30A further illustrates an embodiment utilizing a toggle lock with the handles, similar to locking pliers, which are known in the art. FIG. 30B illustrates a similar embodiment where a snap clamp configuration can be used to lock the arms in place.

The hemostatic clamp of the subject invention is relatively safe and easy to use. However, it can be advantageous to provide with the device a description that outlines the series of steps for successfully completing a procedure utilizing the hemostatic clamp. In one embodiment, written instructions are provided with the device. In an alternative embodiment, instructions are provided in a digital or videographic medium that can be viewed prior to conducting a procedure. In a specific embodiment, a visual presentation of a procedure utilizing the device can be accessible through the World Wide Web (WWW). In a more specific embodiment, the procedure can be presented in the form of a podcast that can be made available through the WWW.

Polydactylism is a congenital defect that is often addressed with the use of suture ligation, particularly in infants; however, this method is not always reliable and can result in neuromas or incomplete necrosis of the tissue, as shown in FIGS. 4 and 5. The devices of the subject invention provide an alternative method for treating polydactylism quickly and with minimal pain or scarring.

Following is an example that illustrates one procedure for practicing the invention. This example should not be construed as limiting.

EXAMPLE 1

Amputation of a Polydactyl Digit on an Infant

An infant presenting with polydactyly is first examined and, if appropriate, prepared for removal of the digit. The infant is usually allowed to suck on a glucose solution, to distract from and diminish pain prior to the procedure. The area around the affected digit is thoroughly sterilized using Betadyne® or a chlorhexidine solution and dressed with sterile field.

Once a sterile field has been applied, the area near the polydactyl digit is locally anesthetized by infiltrating subcutaneously with 0.1 to 0.2 ml of 1% Lidocaine® proximal to the pedicle of the extra digit and the metacarpo-phalangeal joint.

After sufficient time has transpired for the blockade to take effect, the hemostatic clamp is applied, while applying mild traction on the rudimentary digit, flush with the lateral aspect of the base of the digit. The locking mechanism is engaged to secure the clamp around the base of the digit. The hemostatic clamp remains closed for approximately 3-5 min. and allowed to fuse the opposing skin of the lower pedicular segment of the rudimentary digit in a permanent hemostatic fashion.

After the clamp has been closed on the pedicle for several minutes, the extra digit is cut off using a scalpel. The locking mechanism is then disengaged and the clamp is removed, resulting in a thin translucent strip of fused skin which eventually falls off (see FIG. 5).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein are incorporated by reference in their entirety, including all figures and tables, to the extent they are not inconsistent with the explicit teachings of this specification.

We claim:

1. A tissue clamp device comprising:
  a first arm and a second arm, where each arm has a proximal end, a distal end, and a front surface, wherein the proximal ends of the arms are rotatably coupled and wherein the second arm comprises an outer side that defines an indentation;
  a face on each arm positioned, so that rotation of the arms causes the faces to be brought into compressible juxtaposition;
  a depression in the front surface of each of the at least two arms, such that when the arms are brought in juxtaposition, the depressions align to form a divit; and
  a locking mechanism that forcibly secures the arms in the juxtaposed position, the locking mechanism comprising a rotatable toggle arm having a first end and a second end, wherein the toggle arm first end is rotatably connected to the first arm and the toggle arm second end is rotatably connected to a non-circular spindle comprising a ring handle such that when the toggle arm is positioned across the distal ends of the first and second arms and the spindle rotates in the indentation distally to the second arm, the first and second arms are forced together with the ring handle locked at the distal ends of the first and second arms,
  such that a tissue positioned between the faces and within the divit will be fused when the faces are brought into compressible juxtaposition over the tissue.

2. The device, according to claim 1, further comprising a joint stop that limits the rotation of the first and second arms.

3. A device, according to claim 1, wherein at least a portion of the device comprises a rigid, disposable, plastic material.

* * * * *